US010849675B2

(12) United States Patent
Wallace

(10) Patent No.: US 10,849,675 B2
(45) Date of Patent: Dec. 1, 2020

(54) TREATMENTS METHODS AND PORTABLE SURGICAL DEVICES FOR TREATING NEOPLASTIC AND HYPERPLASTIC CELLS IN THE CERVIX AND OTHER DERMATOLOGICALLY OR SURFACE RELATED DISORDERS

(71) Applicant: William Dean Wallace, Lehi, UT (US)

(72) Inventor: William Dean Wallace, Lehi, UT (US)

( * ) Notice: Subject to any disclaimer, the term of this patent is extended or adjusted under 35 U.S.C. 154(b) by 658 days.

(21) Appl. No.: 15/330,666

(22) PCT Filed: Apr. 29, 2015

(86) PCT No.: PCT/US2015/000053
§ 371 (c)(1),
(2) Date: Oct. 25, 2016

(87) PCT Pub. No.: WO2015/167623
PCT Pub. Date: Nov. 5, 2015

(65) Prior Publication Data
US 2017/0215936 A1    Aug. 3, 2017

Related U.S. Application Data

(60) Provisional application No. 62/125,486, filed on Jan. 23, 2015, provisional application No. 61/985,961, filed on Apr. 29, 2014.

(51) Int. Cl.
*A61B 18/08* (2006.01)
*A61B 18/04* (2006.01)
(Continued)

(52) U.S. Cl.
CPC .......... *A61B 18/082* (2013.01); *A61B 18/04* (2013.01); *A61B 18/08* (2013.01); *A61B 18/10* (2013.01);
(Continued)

(58) Field of Classification Search
CPC .............. A61B 18/082; A61B 18/04; A61B 2018/00178; A61B 2018/00029;
(Continued)

(56) References Cited

U.S. PATENT DOCUMENTS 4,014,343 A * 3/1977 Esty ................... A61B 18/1402
219/233
4,823,791 A 4/1989 D'Amelio et al.
(Continued)

FOREIGN PATENT DOCUMENTS

WO    WO2013/158076    * 10/2013

*Primary Examiner* — Jaymi E Della

(57) ABSTRACT

A portable electrosurgical device (ESD) has a housing, a probe connected to the housing and a heating element connected to the probe for destroying human tissue. The heating element is detachable from the probe and/or the probe with heating element can be detachable from the housing. The user can set a drive signal's electrical characteristics, such as operating frequency, duty cycle, peak voltage and the like for a customized drive signal formed in the ESD based on the heating element used. Memory storage allows for storage of inputted data from a keyboard, downloaded reference documents and information off the Internet from an Ethernet connector that can be displayed for reference on a screen of the ESD. Another even more compact ESD is an integral one-piece portable device having a type of pistol hand-held grip, dis-connectable probe, and a rechargeable, removable battery in the handle provides approximately 30, one-minute treatments on a single battery charge.

20 Claims, 27 Drawing Sheets

(51) Int. Cl.
- *A61B 17/32* (2006.01)
- *A61B 18/00* (2006.01)
- *A61B 90/30* (2016.01)
- *A61B 18/20* (2006.01)
- *A61B 18/14* (2006.01)
- *A61B 17/00* (2006.01)
- *A61B 18/10* (2006.01)
- *A61B 18/12* (2006.01)
- *A61B 90/00* (2016.01)

(52) U.S. Cl.
CPC ..... *A61B 18/20* (2013.01); *A61B 2017/00464* (2013.01); *A61B 2017/00473* (2013.01); *A61B 2017/00734* (2013.01); *A61B 2017/32007* (2017.08); *A61B 2017/320069* (2017.08); *A61B 2018/0013* (2013.01); *A61B 2018/00029* (2013.01); *A61B 2018/00035* (2013.01); *A61B 2018/00178* (2013.01); *A61B 2018/00559* (2013.01); *A61B 2018/00607* (2013.01); *A61B 2018/00642* (2013.01); *A61B 2018/00702* (2013.01); *A61B 2018/00714* (2013.01); *A61B 2018/00815* (2013.01); *A61B 2018/00982* (2013.01); *A61B 2018/00988* (2013.01); *A61B 2018/087* (2013.01); *A61B 2018/1266* (2013.01); *A61B 2018/1495* (2013.01); *A61B 2090/0807* (2016.02); *A61B 2090/306* (2016.02); *A61B 2218/006* (2013.01)

(58) Field of Classification Search
CPC .......... A61B 2017/00473; A61B 2017/00464; A61B 2018/00988; A61B 2017/00734; A61B 2090/0807; A61B 2018/0013; A61B 2090/306; A61B 2218/006; A61B 2018/1495; A61B 2018/087; A61B 2018/00982; A61B 2018/00815; A61B 2018/00714; A61B 2018/00642; A61B 2018/00607; A61B 2018/00559; A61B 2018/00035; A61B 18/20; A61B 17/320068; A61B 18/08
See application file for complete search history.

(56) References Cited

U.S. PATENT DOCUMENTS

| | | | |
|---|---|---|---|
| 5,391,144 A * | 2/1995 | Sakurai | A61B 17/22012 601/3 |
| 5,472,442 A * | 12/1995 | Klicek | A61B 18/1482 606/34 |
| 5,540,683 A * | 7/1996 | Ichikawa | A61B 18/12 606/38 |
| 5,611,798 A | 3/1997 | Eggers | |
| 5,814,043 A | 9/1998 | Shapeton | |
| 6,258,088 B1 * | 7/2001 | Tzonev | A61B 18/1402 200/293.1 |
| 6,544,210 B1 | 4/2003 | Trudel et al. | |
| 2002/0095199 A1 * | 7/2002 | West, Jr. | A61B 18/148 607/101 |
| 2005/0015080 A1 * | 1/2005 | Ciccone | A61B 18/08 606/30 |
| 2005/0159745 A1 * | 7/2005 | Truckai | A61B 18/1442 606/51 |
| 2005/0177151 A1 * | 8/2005 | Coen | A61B 18/1492 606/41 |
| 2006/0241589 A1 * | 10/2006 | Heim | A61B 18/1402 606/48 |
| 2008/0147058 A1 * | 6/2008 | Horrell | A61B 18/1402 606/37 |
| 2008/0255607 A1 | 10/2008 | Zemlok | |
| 2009/0062786 A1 | 3/2009 | Garito et al. | |
| 2009/0062791 A1 | 3/2009 | Lee et al. | |
| 2009/0156958 A1 * | 6/2009 | Mehta | A61B 18/203 600/549 |
| 2009/0222001 A1 | 9/2009 | Greeley et al. | |
| 2009/0248019 A1 | 10/2009 | Falkenstein | |
| 2010/0114095 A1 * | 5/2010 | Janssen | A61B 18/1477 606/41 |
| 2011/0046620 A1 | 2/2011 | Lewandowski et al. | |
| 2011/0054460 A1 * | 3/2011 | Gilbert | A61B 18/1233 606/33 |
| 2011/0166563 A1 * | 7/2011 | Cheng | A61B 18/082 606/30 |
| 2011/0172660 A1 * | 7/2011 | Bales, Jr. | A61B 18/1206 606/45 |
| 2011/0276113 A1 * | 11/2011 | Cybulski | A61B 18/042 607/101 |
| 2011/0288543 A1 * | 11/2011 | Cheng | A61B 18/1233 606/41 |
| 2011/0319889 A1 | 12/2011 | Conley et al. | |
| 2012/0136285 A1 | 5/2012 | Korb et al. | |
| 2012/0232547 A1 * | 9/2012 | Cohen | A61B 18/1492 606/34 |
| 2013/0079763 A1 | 3/2013 | Heckel et al. | |
| 2013/0177695 A1 | 7/2013 | Podhajsky et al. | |
| 2013/0204243 A1 * | 8/2013 | Newkirk | A61B 18/1206 606/34 |
| 2013/0267787 A1 * | 10/2013 | Warnock | A61B 18/1402 600/249 |
| 2013/0274734 A1 | 10/2013 | Maass et al. | |
| 2014/0081256 A1 * | 3/2014 | Carmel | A61B 18/18 606/33 |
| 2014/0094786 A1 * | 4/2014 | Keller | A61B 18/1445 606/30 |
| 2014/0276770 A1 * | 9/2014 | Ellman | A61B 18/1477 606/34 |
| 2015/0094703 A1 * | 4/2015 | Zikorus | A61B 18/04 606/27 |
| 2015/0305798 A1 * | 10/2015 | Garito | A61B 18/1206 606/37 |

\* cited by examiner

| MODE OF APPLICATION (MODALITY) | WAVE FORM | APPLICATION TECHNIQUE AND BIOLOGICAL EFFECT |
|---|---|---|
| Electro-fulguration | Damped sine wave form | No electrode-membrane contact; arc from electrode tip to membrane; Mono-terminal |
| Electro-desiccation | Damped sine wave form | Electrode-membrane contact; Mono-terminal |
| Electro-coagulation | Moderately Damped | Electrode-membrane contact; Bi-terminal |
| Electro-section Pure Cut | Pure sine wave | Electrode-membrane contact; Bi-terminal |
| Electro-section Blend | Modulated sine wave | Electrode-membrane contact; Bi-terminal |

(A)

Resistance of Element in Ohms

| | | \multicolumn{7}{c}{Rated wattage} |
|---|---|---|---|---|---|---|---|---|

| | | 20 | 30 | 40 | 50 | 60 | 70 | 80 |
|---|---|---|---|---|---|---|---|---|
| Rated Voltage | 10 | 5.0 | 3.3 | 2.5 | 2.0 | 1.7 | 1.4 | 1.3 |
| | 12 | 7.2 | 4.8 | 3.6 | 2.9 | 2.4 | 2.1 | 1.8 |
| | 15 | 11.3 | 7.5 | 5.6 | 4.5 | 3.8 | 3.2 | 2.8 |
| | 18 | 16.2 | 10.8 | 8.1 | 6.5 | 5.4 | 4.6 | 4.1 |
| | 20 | 20.0 | 13.3 | 10.0 | 8.0 | 6.7 | 5.7 | 5.0 |

(B)

| Parameter | Value |
|---|---|
| Frequency/power @ Port 1 | 14.50 GHz/ >+10dBm |
| Frequency/power @Port 2 | 14.45 GHz/> +10dBm |
| Frequency/power @Port 3 | 40 MHz/> +8dBm |
| Frequency/power @Port 4 | 50 MHz/> +8dBm |
| Frequency accuracy | < +/-1kHz over temp and supply voltage |
| Frequency ageing (first year) | < +/- 0.3ppm |
| Frequency ageing (ten years) | < +/- 2.5ppm |
| Discrete spurious (all ports) | <-70dBc |
| Pulling | 1.5:1 VSWR will not break lock |
| Harmonics | <-20dBc |
| Phase noise @ 10kHz | < 100dBc/Hz |
| Operating temperature | 0°C to 50°C (baseplate) |
| DC power supply requirements | +15V +/-0.5V 1A steady state, 1.5A surge |

| WAVEFORM | TISSUE USAGE | SECTIONING | LATERAL COAGULATION | HEAT | WAVEFORM ON OSCILLOSCOPE |
|---|---|---|---|---|---|
| Fully rectified filtered | pure cutting | excellent | minimal | least | |
| Fully rectified | cutting with hemostasis | very good | very good | more | |
| Partially rectified | coagulation on soft tissue | very poor | excellent | slightly greater | |
| Fulguration | superficial destruction and coagulation near bone | none | excellent for osseous surgery | greatest | |

Fig. 8

CO2 LASER WAVEFORMS

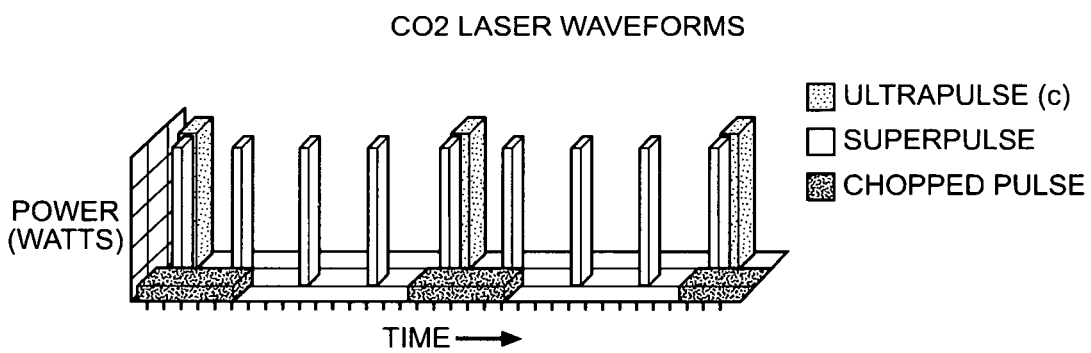

■ ULTRAPULSE (c)
☐ SUPERPULSE
▨ CHOPPED PULSE

NOTE: Each of these laser waveforms is producing the same average amount of power (measured in Joules) but the peak wattage and duration of the pulse vary.

Fig. 9

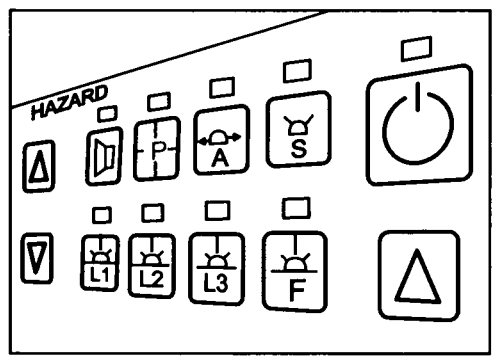
(A)
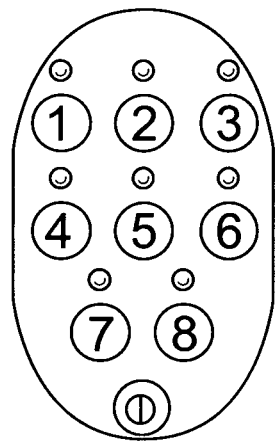
(B)
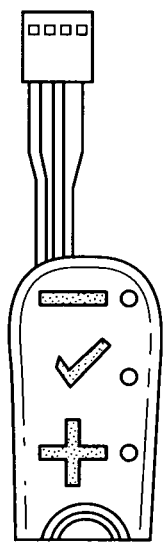
(C)
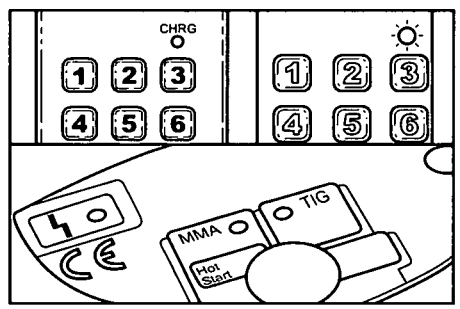
(D)
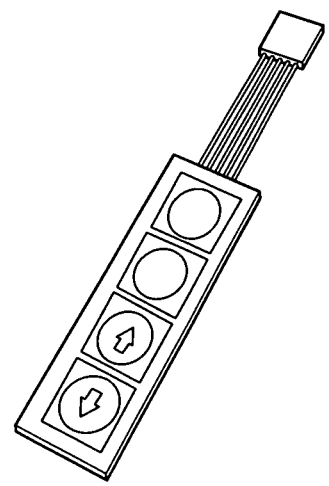
(E)
Fig. 15

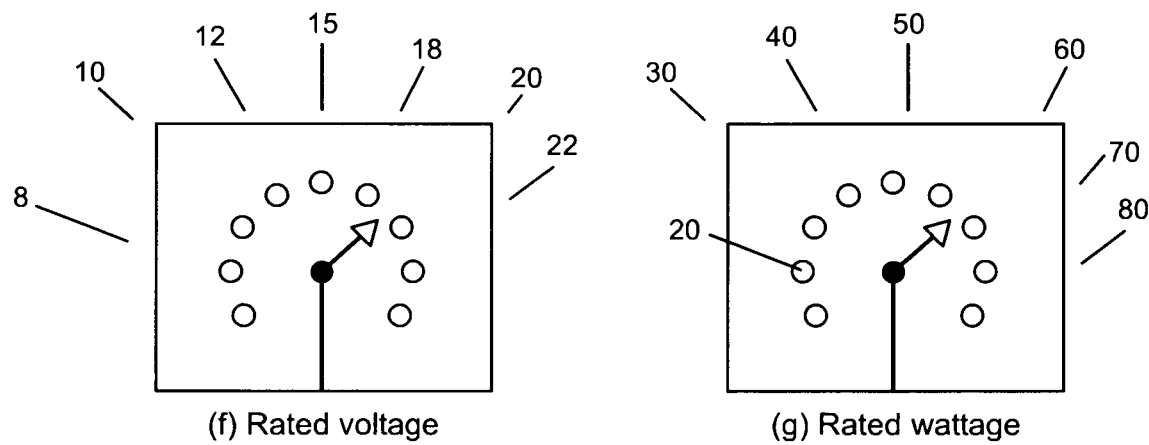
(f) Rated voltage
(g) Rated wattage
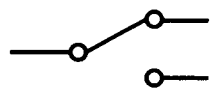
(h) bipolar or monopolar?
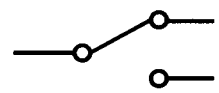
(i) auto-smoke evacuation?
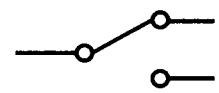
(j) cool down mode?
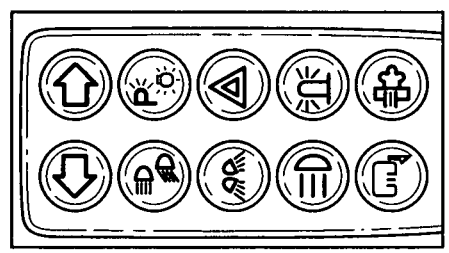
(k) two column array
Fig. 19B

TREATMENTS METHODS AND PORTABLE SURGICAL DEVICES FOR TREATING NEOPLASTIC AND HYPERPLASTIC CELLS IN THE CERVIX AND OTHER DERMATOLOGICALLY OR SURFACE RELATED DISORDERS

This application claims priority the U.S. Provisional Application 61/985,961, filed Apr. 29, 2014, and U.S. Provisional Application 62/125,486, filed Jan. 23, 2015.

Cervical cancer is a serious and growing global health issue. In 2008, there were an estimated 529,000 new cases of cervical cancer and approximately 274,000 deaths, making it the second most common cancer in women. About 88% of deaths occurred in developing countries, of which 53,000 occurred in Africa, 31,400 in Latin America, and the Caribbean, and 159,800 in Asia. In Eastern Africa, South-Central Asia, and Melanesia cervical cancer is the most common cancer killer of women. (Ferlay J., Shin H R, Bray F, Forman D, Mathers C, and Parkin DM, GLOBOCAN 2008 v1.2, Cancer Incidence and Mortality Worldwide, IARC CancerBase No. 10 [online database]. Lyon, International Agency for Research on Cancer, 2010 (http://globocan.iarc.fr).

Although it affects women worldwide, cervical cancer mortality is highest in low-resource settings where women have not traditionally had access to organized screening programs. Human papillomavirus (HPV) is a group of viruses that are extremely common worldwide. There are more than 100 types of HPV of which at least 13 are cancer causing. Cervical cancer is caused by sexually acquired infection with certain types of HPV. Infection with HPV is preventable through vaccination but the vaccine should be given prior to infection, which often occurs within a few years, of sexual debut. For those women already infected, development of cervical cancer is preventable using relatively simple, low-cost screening and treatment approaches that can be implemented at the district, if not primary, health care level. Treatment of cervical cancer lesions can be done by 1) excision with hysterectomy, electrosurgical needle conization, cold-knife conization, laser conization ($CO_2$), large loop excision of transformation zone (LEEP, LLETZ), or by 2) tissue ablation (destruction) by radical diathermy (electrocautery), electrocoagulation diathermy, electrofulgaration, cold (thermal) coagulation, cryotherapy, and laser vaporization ($CO_2$).

One method of treating cervical cancer is the removal of the cancerous cells.

Electrosurgical medical care describes a number of different procedures by which electricity is used to cause thermal destruction of tissue. There are two basic types of electrosurgical medical care commonly used and that are relevant to the matters of this disclosure: high frequency electrosurgical treatment and electrocoagulation.

High frequency electrosurgical treatment refers to four different methods, electrocautery, electrodessication, electrofulguration, and electrosection, wherein each involves using a handheld instrument, a "probe," to pass high-frequency current through tissue where the current is converted to heat as it passes through the tissue's resistance. The result of the heat buildup within the tissue is the destruction of the tissue.

Electrocoagulation is a form of a direct transfer of heat to tissue. Instead of passing electrical current through the tissue, the current is used to heat a heating element of the handheld instrument, which is then applied to the tissue. This form of electrosurgical medical care is most commonly used for procedures such as hemostasis and tumor destruction when high-frequency electrosurgical treatment is not advisable or causes destruction or ablation of the tissue.

Because there are a multitude of different heating elements, signal waveform shapes, time and duty cycle variations and power levels for operating, all depending on a particular procedure and tissue at hand, it is of the greatest importance that an electrosurgical device (ESD) operate with the precise type of attachments, such as probe, heating element and probe tip, and of operating characteristics based on, for example, the heating element being used, in order to perform the medical procedure with optimal results. Dangerous side effects to be avoided, and that become risky without using the exact components and operating parameters, are electric shocks, electrical or thermal burns, eye injury (from sparks), transmission of bacterial and viral infections and implantable device malfunction. These conditions, if allowed to be created during the procedure, inject complications that can run from temporal to permanent injuries.

Regrettably, there are many areas of the world without the adequate infrastructure to treat cervical cancer or neoplastic cells in their early stages. Most or virtually all equipment needed to treat abnormalities in cervical cell growth require electricity and [and] in many parts of the world, there are no reliable sources of electricity. Furthermore, trucking in a variety of bulky medical equipment or consumables is impractical, as many of these same parts of the world do not have reliable roads.

BRIEF DESCRIPTION OF THE DRAWINGS

The accompanying drawings, which are incorporated herein and form a part of the specification, illustrate one or more embodiments of the present disclosure and, together with the description, further serve to explain the principles of the disclosure and to enable a person skilled in the pertinent art to make and use the disclosure.

FIG. 7 (A)-(C) illustrates various types of documents that can be stored in memory of the ESD for easy reference by the user.

FIG. 8 illustrates both the type of reference laser cutting information that can be stored in memory of the ESD for easy reference by the user, and the different variations in the laser signal waveforms used in electrosurgical medical care.

FIG. 9 is a plot for a laser heating element of power versus time for certain laser waveforms.

FIGS. 15(A)-(E) present pictures of five types of membrane switches with LED light indicators usable in of the disclosed ESD

FIGS. 19(A)-(B), including FIGS. 19(a)-(k), depict various switches in the ESD according to one aspect of an embodiment.

DETAILED DESCRIPTION OF THE DISCLOSURE

For the purpose of clarification, descriptions are provided for (I) the field of electrosurgical medical care in general, (II) exemplary types of heating elements for electrosurgical procedures, and (III) novel features of the disclosed electrosurgical device (ESD).

ESD Housing Components

Figure 1:
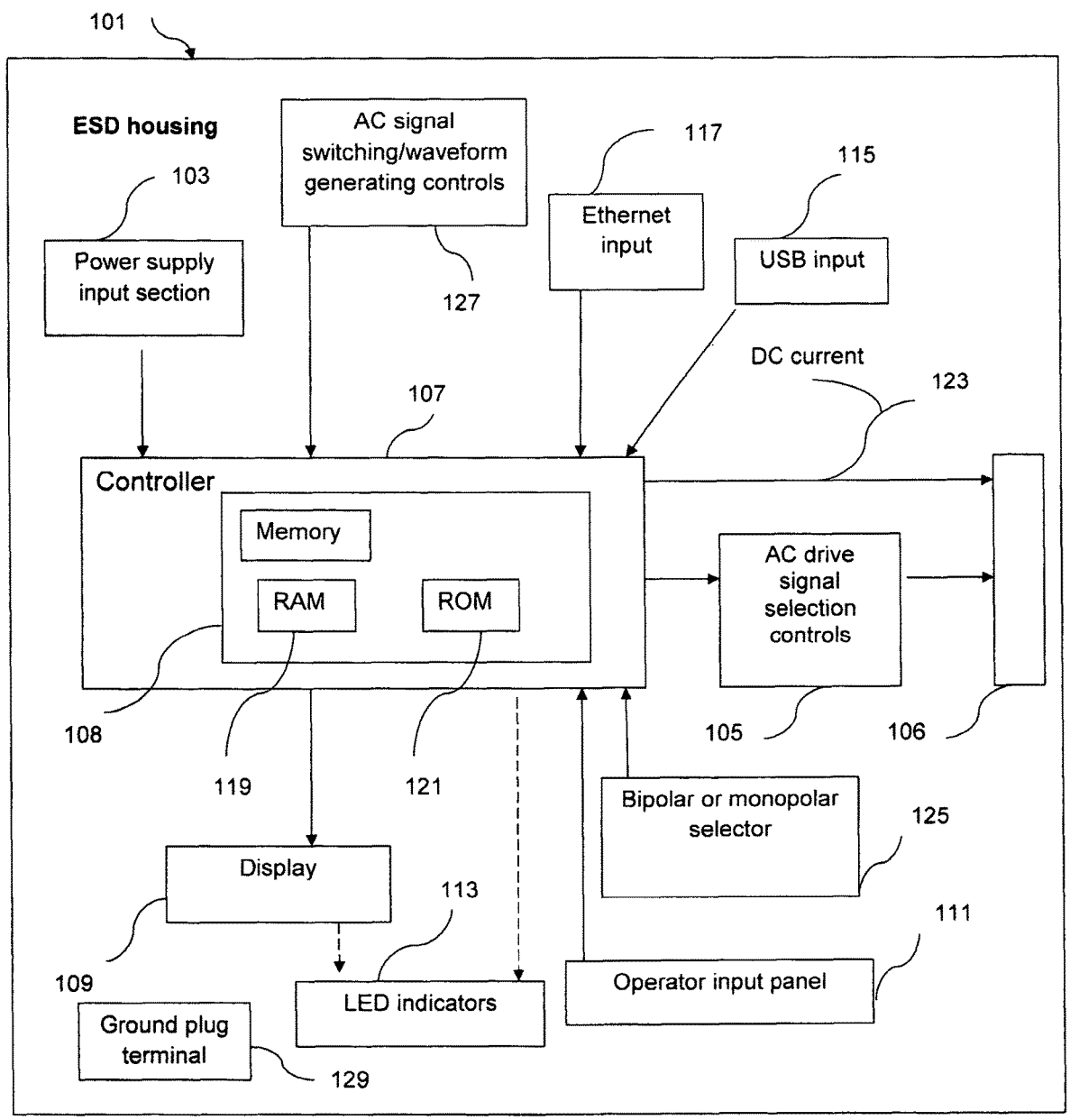
FIG. 1 is a schematic block diagram of the components of an electrosurgical device SESD) housing according to one embodiment.

FIG. 1 shows a schematic block diagram of components contained in the housing of an electrosurgical device (ESD) according to an embodiment. The ESD has a housing 101 which frames the components shown in FIG. 1. For simplicity regarding FIG. 1, housing 101 may be at times referred to as the ESD, although the ESD in total consists of both the housing component and the probe component that is attached to the housing.

FIG. 1 shows a schematic block diagram of components contained in the housing of an ESD according to an embodiment. The ESD has a housing 101 which frames the components shown in FIG. 1. For simplicity regarding FIG. 1, housing 101 may be at times referred to as the ESD, although the ESD in total consists of both the housing components and nthe probe component that is attached to the housing.

A detachable probe (not shown) is connected to the ESD at connector terminal 106. The housing of the ESD also contains electronics that include, in particular, a controller 107, which may also be, or be referred to as, a microprocessor, computer, processor or other one or more calculating and controlling type of devices. Herein, these terms are interchangeable and the component is referred to as a controller. The housing of the ESD also contains a display 109.

Power is supplied to the controller, the display and other components as needed from power supply input section 103. Although not explicitly shown, it is understood that the appropriate DC voltage is supplied and regulated through controller 107 to operate other components of the ESD. Controller 107 generates and outputs a regulated DC or AC signal as needed to the probe and other ESD housing components, such as to display 109 or to operator input panel 111. Input panel 111 may be a keyboard connected to the ESD via a USB input 115 or any other type of user input device. USB input 115 can be used to download guidelines, operating parameters, checklists and the like for a variety of different heating elements for display to the operator. Display 109 may contain, or be separately connected to, other types of one or more displays, such as light emitting diode (LED) indicators 113. The dashed lines to LED indicators 113 are to indicate that the use of other displays or indicators, in addition to display 109, is an option.

Additionally, DC voltages are used within controller 107 for setting electrical parameters associated with an operator-selected heating element and selections of, and parameters chosen by, the user associated with the heating element being used. Ethernet input 117 on the ESD enables a user to access other information sources as needed when in remote areas. Controller 107 contains memory for information storage that includes one or more RAM 119 and ROM 121 memory units. The ESD contains AC drive signal selection controls 105 containing one or more selector knob controls for selection of heating element types and operating signal characteristics of the drive signal sent from the ESD to the probe.

Bipolar or monopolar selector 125 is for the user to select whether it is working with a one electrode or a two electrode heating element at the point of the tissue targeted in the surgery. Ground plug terminal 129 is the input for the ground conductor used in a monopolar electrosurgical operation. This ground conductor comes from a second electrode placed against the patient's body remote from the surgical site.

In one embodiment, in addition to the AC drive signal, DC current is outputted as required along path 123 from controller 107. Probe connector 106 is where the signals are outputted from the ESD housing and is where the probe of the ESD is connected to ESD housing 101.

ESD Probe with Heating Element and Probe Tip Components

The probe has a probe shaft at a distal end of which there is a probe tip. The probe may have an integral fixed probe tip or the tip may be removable. The probe shaft is the section that the user grasps when using the probe. Herein at times the probe shaft is referred to simply as the "probe" or the "instrument." The probe shaft may be formed as a straight structure, or have an angled shape or be formed with a handle that is formed with a more acute angle to a straight or angled part of the probe known as the probe shaft.

Figure 2:
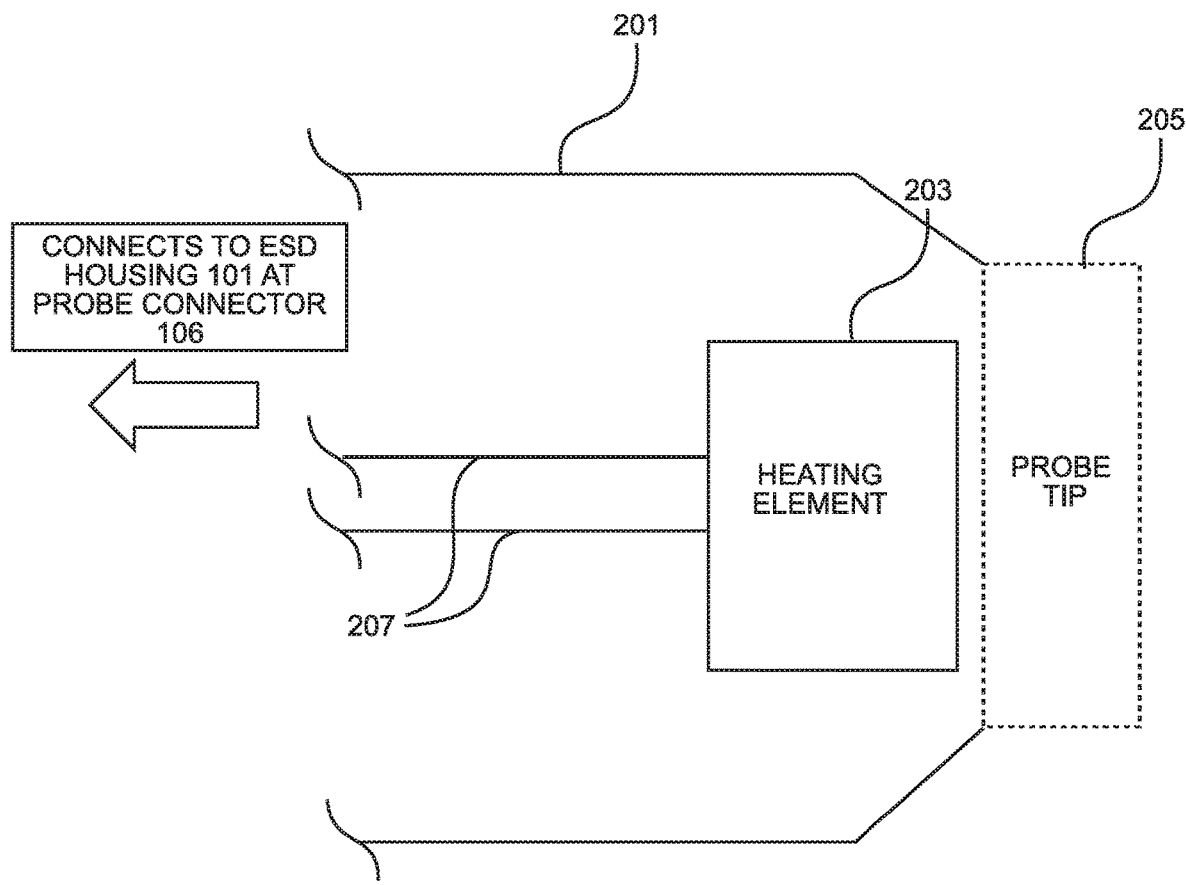
FIG. 2 is a simplified schematic that shows the heating element and probe tip at the surgery-site end of the probe.

FIG. 2 is a simplified schematic that shows the heating element and probe tip at the surgery end of the probe. In FIG. 2, a probe 201 has a heating element 203 and a probe tip 205 mounted at an end of the probe that is closest to the surgery site, which would be to the right of probe tip 205 (the surgery site is not shown in FIG. 2). While only the portion of probe 201 necessary to show the relationship of heating element 203 and probe tip 205 is shown, the left side of FIG. 2, if extended, would show the other end of probe 201 being connected to the housing of the ESD at a probe connector on that housing. Specifically, probe 201 is a detachable probe and is connected to probe connector 106 in ESD housing 101 shown in FIG. 1.

Probe tip 205 is shown in dashed lines because it may or may not be used. Heating element 203 is positioned closely next to probe tip 205 and serves to heat the probe tip to a high temperature sufficient to destroy the targeted tissue. When probe tip 205 is not used, such as when the heating element electrode is placed in contact with the tissue, the heat is transferred directly from heating element 203 to the tissue and the driving energy transmits through the tissue to either a second electrode as part of heating element 203 (a "bipolar" configuration) or to a ground pad pressed against the patient's skin remote from the surgery site (a "monopolar" configuration). In the monopolar case, a ground conductor external to probe 201 is connected between the ground pad and the ESD housing to complete the circuit path.

Probe tip 205 contains the heating element 203 and provides the surface or projection to the targeted tissue by which the heat generated by a drive signal delivered along conductors 207 to heating element 203 is applied to the tissue. Probe tip 205 and/or heating element 203 may be detached and replaced with a different heating element, or, in another embodiment, the combination probe tip and heating element is replaced with a different combination probe tip and heating element. The two components may be a single unit or may be separate units. Alternatively, this modification of an off-the-shelf probe allows for manual replacement of heating elements of different types and component values and probe tips of different shapes.

With this replacement feature of the components at the surgical end of the probe, there is no need to detach and replace the entire probe itself or to pull out an entirely new ESD to get the most precise heating element/probe tip combination desired for the electrosurgical treatment at hand.

Controller Components

Figure 3:
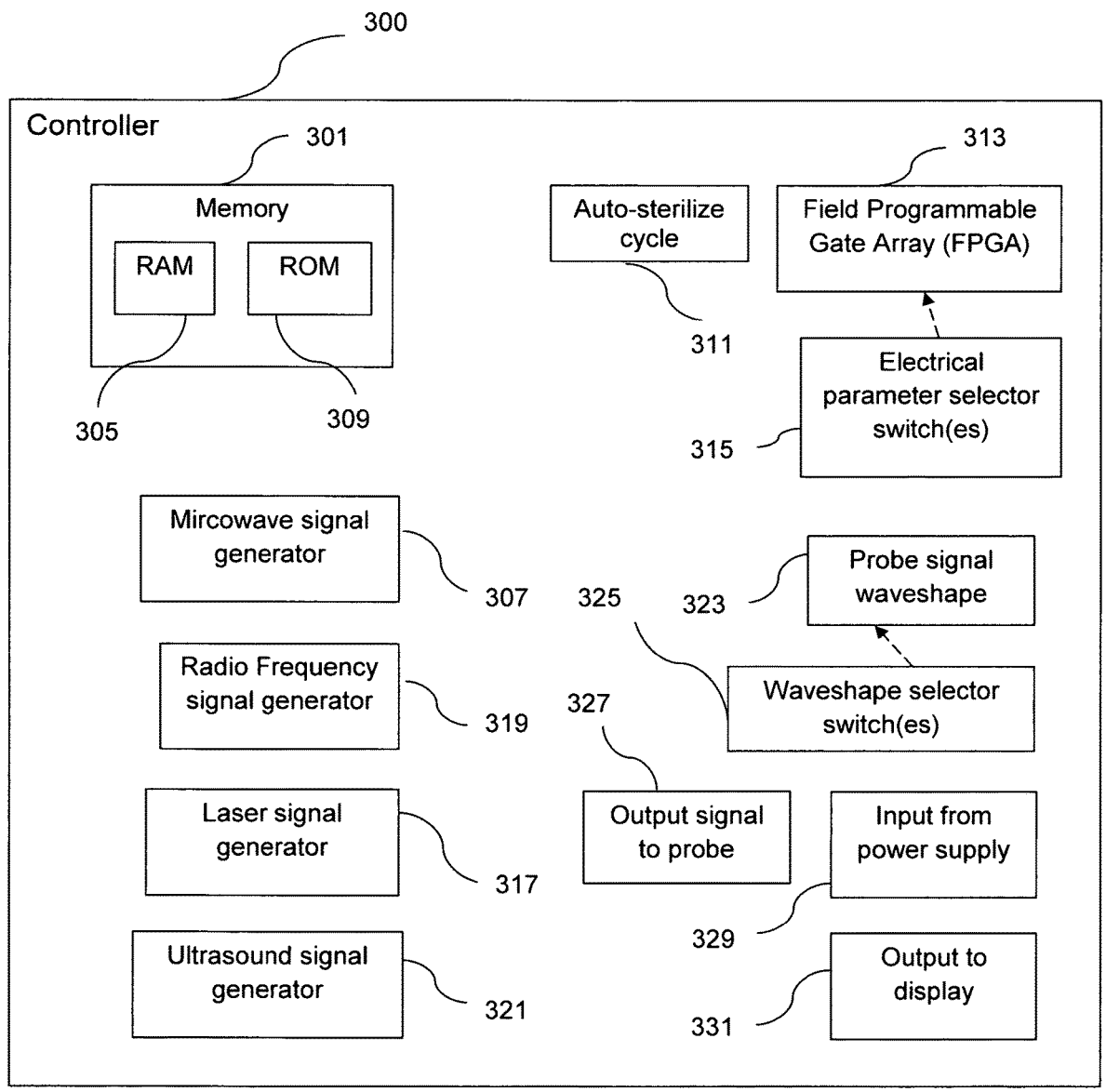
FIG. 3 is a schematic block diagram showing components of the controller.

FIG. 3 is a schematic block diagram of the controller. It is understood that the controller may also be referred to, and operate the same as, a microprocessor, a computer or other equivalent calculating and controlling component. Also in one embodiment, the controller comprises more than one interconnected controller, microprocessor or computer and the like.

With reference now to FIG. 3, a controller 300 contains a memory 301 that has a random access memory (RAM) 305 and a read only memory (ROM) 309 for storing data and documents and for retrieving information from memory storage for display to the user.

In one example or embodiment, the controller includes or has access to separate modules for connecting to various signal generators to correspond to frequencies and wave shapes usable in the ESD. This includes, for example, a microwave signal generator 307, a radio frequency signal generator 319, a laser signal generator 317 and/or an ultrasound signal generator 321. Each signal generator module is operationally coupled to other controller functions, power supplies and inputted information that is used in the selection of a particular signal generator to activate and for activating a signal having certain frequency and other characteristics, such as whether it is rectified, pulsed, has a duty cycle associated with it, is a continuous wave, and other factors such as its peak and/or average voltage power.

Controller 300 also contains, or is operationally coupled to, a field programmable gate array (FPGA) 313 for being programmed in the field by the user to set a signal to the probe having certain signal characteristics. Usable with FPGA 313 is one or more electrical parameter selector switch(es) 315, where the signals from electrical parameter selector switch(es) 315 are sent to either FPGA 313 or elsewhere in controller 300 to be acted on in generating the drive signal from the controller to the probe. Similarly, one or more waveshape selector switch(es) 325 is coupled to a probe signal waveshape generator 323 for further shaping the drive signal to be used in the ESD. Controller 300 receives a power supply input voltage and power at input from power supply 329. Information is projected by controller 300 onto a display 331 to provide viewable information to the user. Display 331 may consist of more than one display. In one embodiment, the display is a touch screen display that also provides a function of switching electrical signals, or in another embodiment is a 6, 8 or x-segment digital display. In one embodiment, an audio converter and output (not shown) associated with the visually displayed data is also be incorporated into the ESD. The output signal from controller 300 to the attached probe is delivered at output signal to probe 327. An auto-sterilize cycle 311, in accordance with one feature of the disclosed novel ESD, is also contained in controller 300 in that the controller regulates the signal and timing associated with the one or more signals for the auto-sterilize cycle.

In another embodiment, controller 300 also contains connections and other items common to controllers, even though not shown. This includes items such as voltage and current regulators and sensors or circuits responsive to sensor inputted data at the controller.

Figure 4:
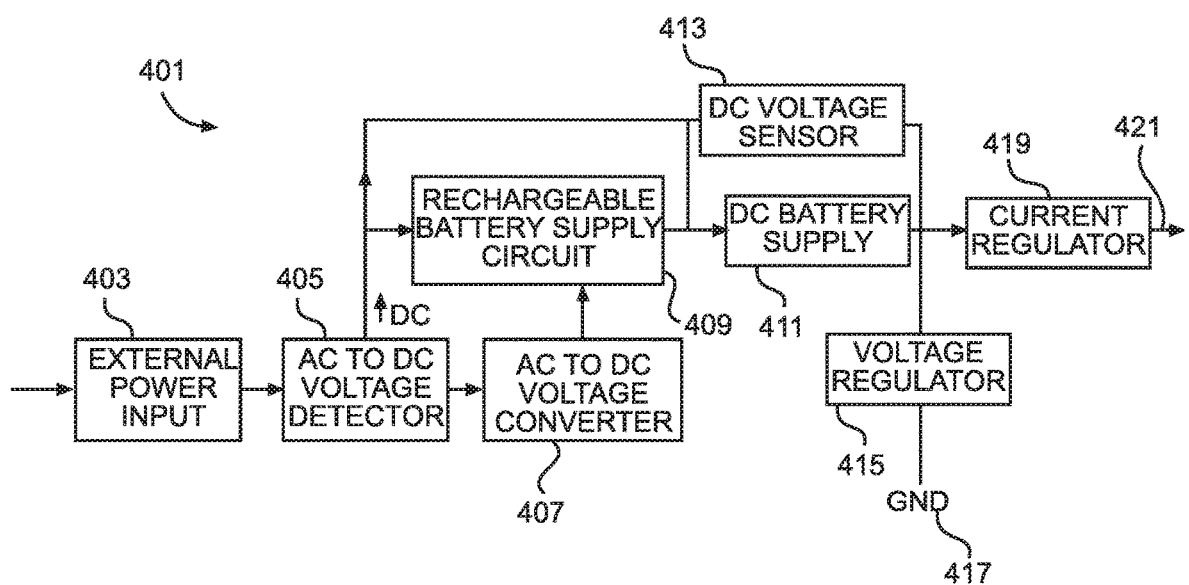
FIG. 4 is a schematic illustrating the power supply circuits according to an embodiment of the electrosurgical device.

The controller's input from power supply 329 in FIG. 3 is able to power the ESD from rechargeable batteries in power supply input section 103 of the ESD housing 101, and, alternatively, is also able to provide the power supply from an external power source when an external source is connected as an input to power supply input section 103. FIG. 4 is a circuit schematic of the power supply input section of the ESD. The concept of the described ESD embodiments is to use a battery source for the ESD, and only use wall power to charge the battery. However, alternative charging is possible from solar cells or stored DC battery recharge power through a DC charging input port.

Advantageously, the design of the disclosed ESD recognizes the need and importance of a power supply in situations where the ESD is used in remote areas, for example where grid electricity is not readily available, and allows for a variety of power supply sources.

Power Supply Unit

In the power supply schematic diagram 401 of FIG. 4, an external power input 403 receives an AC or DC input signal. At AC or DC voltage detector 405, the inputted signal is detected and sensed to be either an AC or a DC signal and includes a signal regulator to protect against excessive voltage signals. If the input signal is detected as being an AC signal, the signal is routed to AC to DC voltage converter 407, where the AC signal is converted to a DC signal with a regulated DC signal output inputted to rechargeable battery supply circuit 409.

If the input signal back at AC or DC voltage detector 405 is detected to be a DC signal, the DC signal is sent directly to rechargeable battery supply circuit 409, and is also fed as an input to DC voltage sensor 413 where the DC voltage is sensed and fed as output to the input of voltage regulator 415, drives a current flow through current regulator 419 and a regulated current is outputted at the output of current regulator 421.

With this arrangement, a DC inputted signal simultaneously charges rechargeable batteries in DC battery supply 411 and provides the DC voltage and current to the controller 300 and other electronics of the ESD. If an AC signal in inputted, the same action occurs with the power supply design of FIG. 4, in that the AC signal is converted to a DC signal and that signal is used to simultaneously supply the voltage and current as the power supply to controller 300 and the electronics of the ESD while also being used to charge the rechargeable batteries. A sensor (not shown) disconnects the recharging of the batteries once they have reached a threshold voltage level.

In an example, a vehicle carries a supply of charged battery packs for use over time during the journey. In another embodiment, solar cell panels are be mounted on the vehicle, be it a car, van or bus as examples, to supply DC power to the ESD and for recharging the external battery packs as well.

Heating Design of the Probe Tip with Positive Temperature Coefficient

A positive temperature material (PTM) refers to a material having a positive temperature coefficient (PTC). Both PTC and PTM are used interchangeably herein to refer to materials or components that contain or are made with a positive temperature coefficient material.

PTM exhibits a resistance reading just like a resistor. The difference with a PTM heating element is that its resistance changes greatly as the temperature changes. When a PTM is in its cold resistance state, that is, when there is no power or low power in the circuit, the atoms making up the PTM ceramic are arranged in a specific pattern that allows some of the electrons to flow about freely. The electrons "carry" the electricity through the part and the more "free" electrons existing the easier electricity can pass through the ceramic. Hence, the PTM is in its low resistance state. However, when the circuit is energized with sufficient power (electricity), the PTM heats up almost instantaneously to its designated transition set point, which may be set, for example, at just above 120° C. When the PTM heats up, its resistance drastically increases. The high resistance of the PTM essentially causes the electricity to cease "flowing" through the component. The resistance of the PTM is able to change drastically because as the PTM heats up, the atoms making up the PTM ceramic re-arrange themselves in a different pattern (hence the name transition temperature) and this new atomic arrangement "locks" the free electrons in place so that they are no longer able to wander about freely in the ceramic.

The inventor of this disclosure has found that, although it is not required, PTC technology offers significant benefits in two key areas of importance in an ESD: safety and efficiency.

Figure 5:
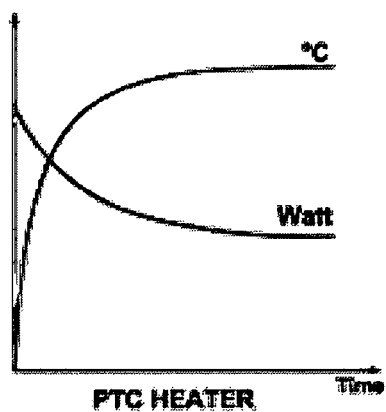
FIG. 5 is a standard plot of temperature versus power over time for a positive temperature coefficient material showing that as temperature increases, power decreases.

A heating element made of PTM is self-limiting in that as the heating element approaches its design operating temperature, electrical consumption is automatically decreased. FIG. 5 is a standard plot of temperature versus power over time for a heater made from a PTC material that shows that as temperature increases, the power decreases.

If the user wants to apply a constant temperature to tissue, a PTC heating element is an advantage because it tends to regulate itself at a constant temperature. This self-regulating property allows PTC heating elements to operate at nearly the same temperature irrespective of variations in the voltage, ambient temperature and changes in thermal load.

Figure 6:
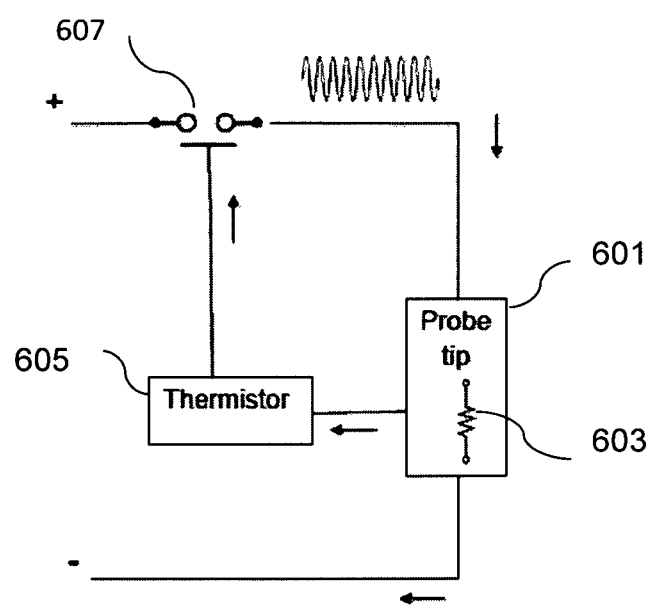
FIG. 6 is a circuit design for heating the probe tip of the ESD according to a positive temperature control heating concept with a thermistor feedback circuit.

The difference between a PTC heating element and a traditional heating element, such as a spiral, wound or coil wire, is that the PTC heating element changes power level automatically in response to ambient or environmental demands. A PTC heating element is incapable of overheating. In addition to the heating element, other temperature-controlled components can also be made of a PTM FIG. 6 shows a circuit design for the heating of the probe tip of the ESD according to a PTC heating concept using a thermistor feedback circuit. The thermistor may or may not be formed with a PTM, but, either way, the thermistor feedback can be used with a PCT heating element component.

In FIG. 6, the probe tip 601 could include a standard resistive element 603, such as a Nichrome wire or a thick film, screened resistive ceramic element with a resistance of 3 ohms, with a 10 volt D.C. power supply from the power supply, which would result in giving 33 watts of power. A feedback control circuit connects a thermistor 605 between the probe tip and the heating element's on-off switch 607 to monitor temperature of the probe tip and turn on and off the voltage of the resistor element in the probe tip so to maintain the probe tip at a desired temperature, such as at 120° C.

Although not required to enable the disclosed ESD, the PTC concept for the heating element control provides an additional safety mechanism for assuring that the probe tip does not get into a run-away heating mode, due to, say, a failure of the thermistor control circuit, by making the resistor element with a PTM. In one embodiment, this serves as either a simple control mechanism by maintaining the PTC control point at a specific probe tip temperature setting, such as at 120° C. without need for a thermistor, or in another embodiment, a PTM serves as a safety mechanism with a thermistor to assure that the probe temperature does not get too high.

Thus if a thermostat, temperature setting or a temperature control component of the ESD fails while in the ON setting, or a cooling fan (if used) fails, the heating element will automatically reduce the power to a minimum operating level without overheating, while the surgical unit remains operational. If there is a sudden thermal load placed on the heating system as may occur when the tip comes into contact with human tissue, the PTC heating element automatically increases its heating power to replace the heat loss. This gives a precise temperature control during the procedure for a higher level of accuracy of the surgical instrument unit. As soon as the excision of the tissue has been accomplished, the heating element will stabilize again at a lower power level, analogize to it going back to a "treading water" mode. The heating element system of the ESD can use a PTC-based heating element and a thermostat; or, the thermostat can be eliminated entirely and let the PTC control the temperature.

In one embodiment, the PTC heating element draws full rated power upon startup to quickly heat the element, and reduces power consumption as operating temperature is reached. The heater only works as hard as it has to in order to maintain temperature. This saves energy and achieves a more consistent temperature control, to give more precise cutting of tissue with the ESD using PTC.

PTM in Ceramic Heating Elements

In some embodiments, ceramic heating elements are constructed from PTC ceramic materials. PTC ceramic materials comprise thin films of ceramics (some barium titanate and lead titanate composites as examples) having a highly nonlinear thermal response, so it becomes extremely resistive above a composition-dependent threshold temperature. This behavior causes the material to act as its own thermostat, since current passes when it is cool, and does not when it is hot. The PTC ceramic material's transition temperature and, therefore, the temperature that the PTC ceramic material heats up to is set by modifying the composition of the ceramic. As an example, one type of a PCT ceramic material is manufactured by General Electric Company has a range of transition temperatures from 60° C. to 140° C. in roughly 10° C. increments.

For transition temperatures of from approximately 60° C. to 140° C., the PTC ceramic material resistance range changes from 0.8 to 1,000 ohms, and the voltage range changes from 10 up to 1000 volts. 10 V up to 1000 V, In one embodiment, the ceramic disc has a diameter of from 2.5-19 millimeters and a thickness of from 1-4 millimeters.

A Detachable and Selectable Heating Element or Probe Structure Overcomes the Problem of not Having the Right Heating Element The ESD disclosed allows for providing a detachable probe and replaceable heating elements allowing for the correct heating element need in the field. The probe for the particular medical procedure is selected by the user and is then attached to the ESD housing. In addition, for a resistance heating element probe, the resistor component is replaceable or substitutable in that a different value can be substituted for another value. For example, a 34-ohm resistor as the heating element in a probe can be replaced with a 30-ohm resistor component, which may be desired to give a different power setting for a different heating setting to be applied to the targeted tissue.

In another embodiment, instructions, specifications, drop-down lists and checklists for any probe are downloadable into the ESD and by use of the RAM and ROM memories in the controller, can be pulled up and shown on display 109 for instant reference by the user. In a further embodiment, the operator inputs data, such as notes, checkpoints, etc. into the memory storage for pull-up when using a particular probe as another form of reference material for that probe type. The memories or storage components in the controller, including the RAM and ROM, are operationally connected to a USB port for downloading and updating this information into the ESD for storage in the memory components.

As one example, a user uses AC drive signal selection controls 105 (FIG. 1) to set the ESD to the type of heating element attached to the probe 201 (FIG. 2). Controller 107 sets the generation of the appropriate drive signal for the heating element and the signal information is presented on display 109. In one embodiment, the heating element is cross-referenced to its related information stored in memory 108. For example, a specification, instruction or checklist is pulled up that has a checklist, operating tips or other operating information associated with that particular heating element. Examples of such information are operating time, temperature and distance or contact-to-tissue information associated with the heating element. This gives the operator the ability to not only select the optimal heating element for a given procedure at hand, but also to view reference material associated with that particular heating element.

For example, a ceramic ultrasound heating element is attached to the probe. The user pulls up a related checklist and operational guidelines for a ceramic ultrasound heating element and finds that, based on the type and location of the tissue to be targeted, decides that this is not the best type of heating element to use. Without changing the ESD or even the probe, the user just detaches the ceramic heating element and attaches an ultrasound vibration heating element, then sets AC drive signal selection controls 105 to ultrasound vibration as the heating element on the ESD. Its drive signal parameters are then displayed on display 109. Again, the user is able to refresh his knowledge of guidelines and factors to consider by reference to a checklist and the like for this newly attached heating element.

In another embodiment, the operator calls up a particular procedure for display by inputting an associated procedure name, such as from those listed above herein, or a tissue type being targeted by the procedure, and in response, a suggested list of heating element(s) and operational parameters, are displayed, such as power level, time intervals for the procedure, current type, duty-cycle characteristics, waveforms (e.g., rectified AC signal, duty cycle setting, pulsed DC signal), and the like.

As another example, the user may wish to lower an operating power level based on the user's assessment of the displayed information associated with the type of connected probe. The ESD housing incorporates an input section whereby a new value of the heating element can be used, with the characteristics and information associated with the new value being displayed on the screen for the operator's further assessment. As examples, in a resistor heating element probe, the displayed manufacturer's information shows use of a 40 ohm resistor element to give a certain heat or power level for use with a certain type of tissue and/or certain dimensions of the target tissue. Alternatively for a ultrasound probe, the displayed manufacturer's information might show a user selection of frequencies for differing surgical procedure conditions. Accordingly, in such an embodiment, the user uses a switch setting to select a certain ultrasound frequency for the ultrasound probe. Similar selections can be made for waveform shapes, time, current values and other operating parameters.

FIGS. 7(A)-(C) illustrate various types of documents that can be stored in memory for easy reference by the user of the ESD. This ready availability of this type of information while the user is on-site of a pending surgery gives a good resource and checklist for quick referral as needed. FIGS. 7(A)-(C) show different types of tables that give summary checklists and operating data for different procedures and conditions.

Other document types, such as checklists, textbook segments, and articles provide medical references that give the user a handy resource to use for reviewing any type of procedure, practice guidelines and expert write-ups on specific aspects of electrosurgery conditions that might be encountered. This is especially useful in providing treatments in remote, out-of-the-way areas.

In one embodiment, these types of documents are downloaded into the ESD by use of the USB input 115 or the Ethernet input 117 for downloading from a web site, and can receive a mouse, a keyboard or any other type of input device. In another embodiment, wireless connections are used.

In one example, this information is formatted in the display as a drop-down list in which an identification name and/or number is listed for each heating element type, such as resistance, microwave, radiofrequency, laser, or ultrasound, with associated current and voltage values, waveform type, AC or DC current, time period for power application to the targeted tissue, and the like. A transfer to the operating guideline or checklist for a particular heating element is projected by, e.g., double-clicking on the line in the drop-down list, or activating another type of switch to project the change of information onto the display screen. In one embodiment, transfer back to the drop-down list is performed by another double-click or use of another activator switch to return to the drop down list. The transfer between screens projecting different information is a matter of design choice.

In another embodiment, in addition to USB input 115, Ethernet input 117 allows for connection to the Internet for displaying of information from the Internet onto display 109. This feature is useful when use of the ESD is in a far remote area and a need arises to get specific information on a certain procedure, on a certain heating element, to connect with another medical expert, and the like. In one embodiment, a dish or other receiving antenna and a proper interfacing circuit (box) are used if the location is in a far remote area without cable internet access.

Controller 300 (FIG. 3) contains memory that includes ROM 309 and RAM 305 used in storing programs, applications, historical data, drop-down lists, as examples, and retrieving information in conducting operations of the device.

Display 109 (FIG. 1) displays information associated with the operation of the device, such as items previously mentioned, battery status indicators, and includes, either integrated in the display or around a boarder of the display, or positioned elsewhere on the device, light indicators, such as LED indicators 113. The light indicators may optionally also have color indicators. LED indicators 113 show the states and operating status of various functions and parameters associated with the device and a current procedure being performed or heating element being used. Display 109 may also display additional information as further described in this disclosure, including images, video, web sites, user input, and so forth.

Operator input panel 111 is usable for user input of information, such as activating a search mode to search memory for certain types of heating elements as just one example of user-inputted information. The user can also input parameter changes to certain types of heating elements.

In one embodiment, in computing a parameter, such as a power setting for the ESD, the resistance of a resistive heating element for control of current is made up of a discrete resistor component in series with the target tissue which has its own resistance, so that the total resistance is the tissue resistance plus the discrete resistor if one is used in the heating element. Resistance of human tissue varies, such as running from 400 ohms for muscle, 2000 ohms for fat and up to 100 KΩ for callused dry skin as some examples. If a certain power setting is set to be constant for a procedure, the current and voltage may constantly be changing depending on the varying resistance such as caused by the changing state at any point in time of the target tissue and the changing distance of the probe from the tissue.

The following two equations, incorporated into the controller, allow for determining any of the four listed parameters, namely voltage, current, resistance and power, if other variables are known and entered into the ESD.

Equation (1): $P=VI$
Equation (2): $V=IR$ (Ohm's Law)
Where P=power (watts, W)
V=voltage (volts, V)
I=current (amperes, A)
R=resistance (ohms, Ω)

For example, a heating element may use a 33 ohm resistor at a 12 VDC supply voltage to deliver ~4.4 watts of power to the targeted tissue. For simplicity in this example, the resistance of the target tissue is not considered, with it understood for an exact determination of the total resistance and the current, the tissue resistance would be taken into account.

Using equations (1) and (2) gives:

$I=V/R=12/33=~0.36$ amps=360 ma $P=12\times0.36=4.32$ watts

If the user is, for example, dealing with an enlarged tissue to be targeted, the user may first retrieve, and have presented on the display, related checklist information stored in memory, such as the power setting for various types and sizes of human tissue. From an assessment of this information, the user may want to increase the power to 7.0 watts. The user inputs 7.0 watts into input panel 111 using a selection of a power level for the resistive heating element that can include a resistance component for the target tissue. Controller 107 uses its calculator function that includes Equations (1) and (2) above to inform the user that it needs to increase the voltage for the heating element to ~19.5 volts (volts=7/0.36). Thus, by the user input of known parameters, an unknown parameter is automatically calculated by controller 107 and applied to the probe with, optionally, with the calculated result displayed on display 109.

Although here and elsewhere herein where it is stated that information or data is displayed on display 109, it is understood that this is but one means of display. The data or information can also be displayed separately, such as by use of 7-element numeric displays, a separate text display or any type of other discrete display that may replace display 109 or be used in addition to display 109.

Manually Replaceable Resistor in Heating Element

In another embodiment, another type of related checklist information stored in memory is a database of discrete resistor values for the heating element cross-referenced to the different types procedures and various type of human tissue. If the heating element as manufactured allows for a manually insert-able resistor, then the user uses the retrieved resistor information to manually replace a resistor heating element with the new resistor value needed to achieve a desired operating condition.

Set an Electrical Parameter to Obtain Settings for Other Electrical Heating Element Parameters Thus as the description and examples show, the disclosed ESD enables the user to select a particular variable, then input data for a desired operating value for that particular variable, then activate a switch (such as to "calculate") and the controller will compute and display calculated values to operate at that particular variable setting. The variable parameter is selectable from the parameters of resistance, current, voltage and power, and their relation as defined by equations (1) and (2) above. The calculated values are presented in terms of the remaining parameters or for any one particularly selected remaining parameter.

Temperature Sensor for Temperature as a Controlled Variable

The previous description relates to the setting and determining of electrical parameters for the heating element. A similar procedure is applicable for temperature, which is not an electrical parameter. A temperature sensor at the probe tip area makes it possible to set temperature as another controlled parameter. A temperature control setting variable by the user during a procedure is activated by the user. Temperature control switch, such as a rotatable on/off switch with a linear variable temperature range set based on the degree of knob rotation, is connected to the controller and causes the controller to adjust a voltage or current up or down at the heating element so to increase or decrease the temperature at the heating element. The temperature sensor is positioned at the heating element to sense and transmit temperature data to the controller from which the heating element temperature is displayed on display 109.

If the user selects the temperature as the parameter to be maintained as constant, then the controller uses the received temperature data, and again the relationships of Equations (1) and (2) to, for example, constantly adjust the current to maintain a constant temperature throughout the electrosurgical procedure. In one embodiment, the temperature sensor is based on an output voltage of the sensor wherein the output voltage is indicative of a certain temperature. See, for example, Analog Devices product AD 22100, Voltage Output Temperature Sensor, manufactured by Analog Devices, Inc., Norwood, Ma. The controller adjusts other parameters, such as the voltage or current at the heating element, so to maintain a constant output voltage of the sensor, that is, maintain a constant temperature at the heating element.

User Switchable Heating Element or Probe Type

In another embodiment, if the user wants to change to a different type of heating element, such as from a resistive to a laser heating element, the user activates a drop-down list of heating elements. This would be stored in memory and may consist of medical reference material, manufacture product specifications, medical standards checklists and application notes, and the like. As one example, the user selects a laser heating element. By making that selection, the controller connects to its preprogrammed laser heating element output. In another example, the user selects a resistive heating element, with the displayed literature showing relations for different resistor values to different types of electrosurgical procedures and other parameter recommended values.

As regards a resistor heating element, in another embodiment, the resistor element is manually replaced at the probe tip if this feature is available from the manufacturer or designed as an adaptor into a probe. A change in resistor value may be desired to change the power setting or other operating parameter. In yet another embodiment, different selectable resistor elements are available from a collection of substitutable resistors that come with the manufactured probe or are added as part of the disclosed ESD. The resistive heating element is a single resistance or alternatively consists of more than one discrete resistance in a parallel arrangement, series arrangement or a combination thereof. In yet another embodiment, the resistor element is a thick film resistor formed on a ceramic sheet.

The replaceable feature conserves space, time and costs for the operator as well.

Example: Using an Ultrasonic Heating Element

In another embodiment, the disclosed ESD with an ultrasonic heating element attached to the distal end of the probe (relative to the ESD housing) delivers ultrasonic energy to a blade or mechanical cutting element. A relative low heat is generated when using ultrasound, in combination with a rapid scissor-type cutting element, with the primary energy source being vibration. The power supply and drive signal are sent from the controller and ESD housing to the cutting element, such as a knife or forceps, in the distal end of the probe. The vibration frequency of the cutting element is approximately 55-56 KHz, as one exemplary vibration frequency. This causes the cutting element to cut through the tissue with enough heat to create coagulation of the cut tissue.

Example: Using a Laser Heating Element

In another embodiment, a laser heating element is used. FIGS. 8 and 9 present reference information that can be stored in memory of the ESD for easy reference by the user, including the different variations in the laser signal waveforms used. The waveforms depicted show the different peak amplitudes of the signal, and the variation in dwell time between pulses or duty-cycle settings for the laser signal. It further shows and lists how the waveform can be fully or partially rectified. The table relates the waveforms to the heat generated, evaluates the lateral coagulation and gives notes on the type of tissue usage for the various waveforms.

FIG. 9 is a plot for a laser heating element of power versus time for certain laser waveforms. In particular, FIG. 9 shows the use of a pulsed laser waveform, with a dwell time between pulses. Waveforms are shown for three different types of laser pulses, namely for an ultrapulse, a superpulse and a chopped pulse.

The information presented in FIGS. 8 and 9 are examples of the scope of electrical variable characteristics possible for laser heating elements. The disclosed ESD allows for the user to essentially customize to an extent the operating conditions by being able to set operating parameters such as laser frequency, pulse duration, peak wattage and average power to be used in any procedure. The user is also able to switch to a laser heating element without having to attach a different probe or use an altogether different ESD unit.

Determining Type of Heating Element and Replace Heating Element Cartridge

In yet another embodiment, the probe has replaceable cartridges for the heating element/probe tip available from the manufacturer. In yet another embodiment, an off-the-shelf probe is modified for use with such replaceable cartridges, with the applicable electrical characteristics for that particular cartridge (heating element type) being determined, set, controlled and delivered to the cartridge by the controller. With the replaceable cartridge concept, the same probe stays connected to the ESD housing and only the replaceable cartridge is switched by the user. As examples, only different resistor values can be used in a resistive heating element with replaceable cartridges. A different probe tip mechanical structure can be replaced by using a replaceable cartridge. A user can go to a different heating element by replacing a resistor heating element cartridge with a laser heating element cartridge. Further, the cartridge feature can contain only the heating element, only the probe tip or a combination of the two in a cartridge. In another embodiment of the cartridge and manual replacement features, the user disconnects and switches the probe to change to a different heating element and/or probe tip, while using the same ESD housing unit.

Select Monopolar or Bipolar Operation

Figure 10A:
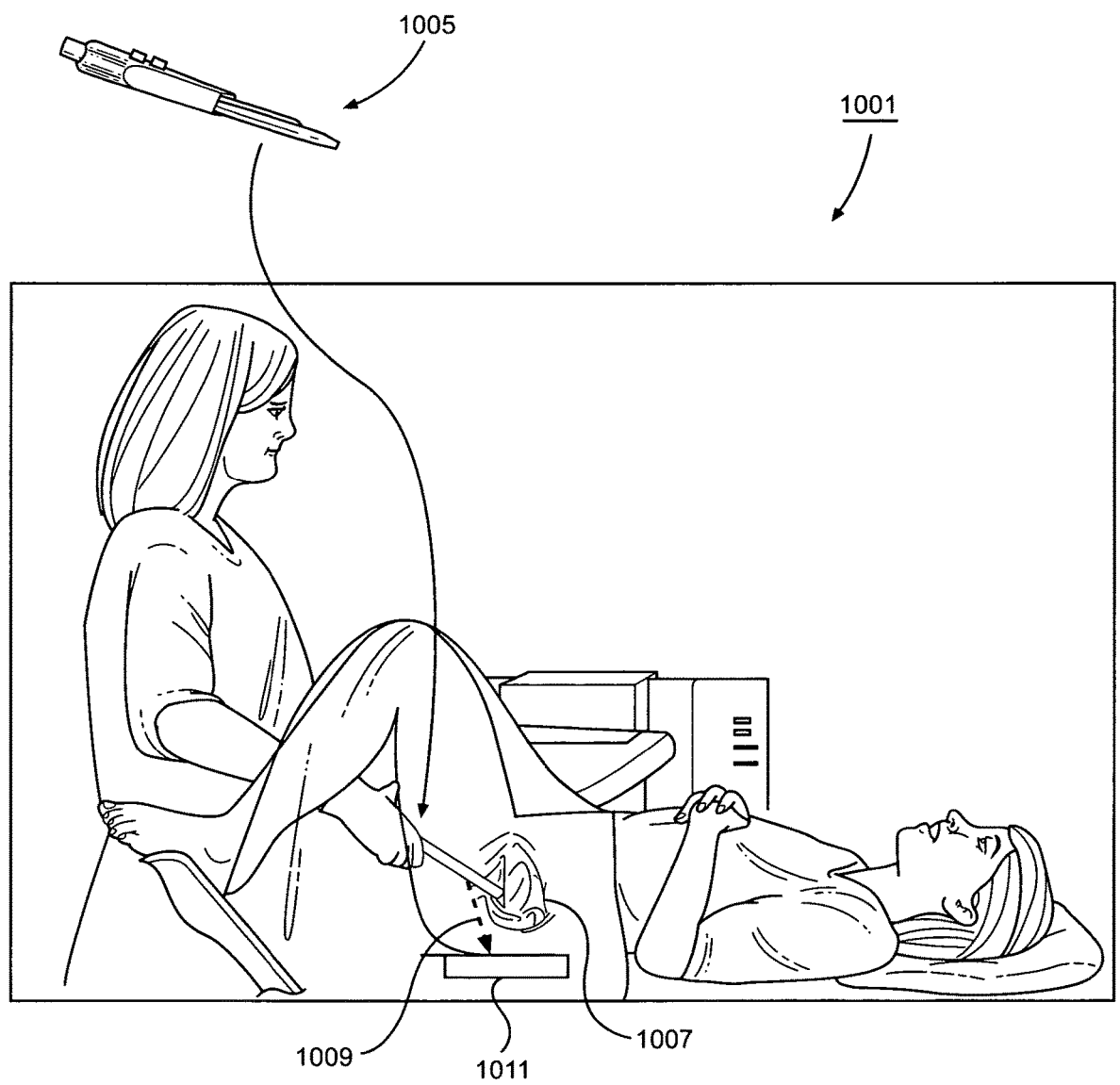
FIG. 10(A) illustrates an arrangement of a monopolar electrosurgical procedure.
Figure 10B:
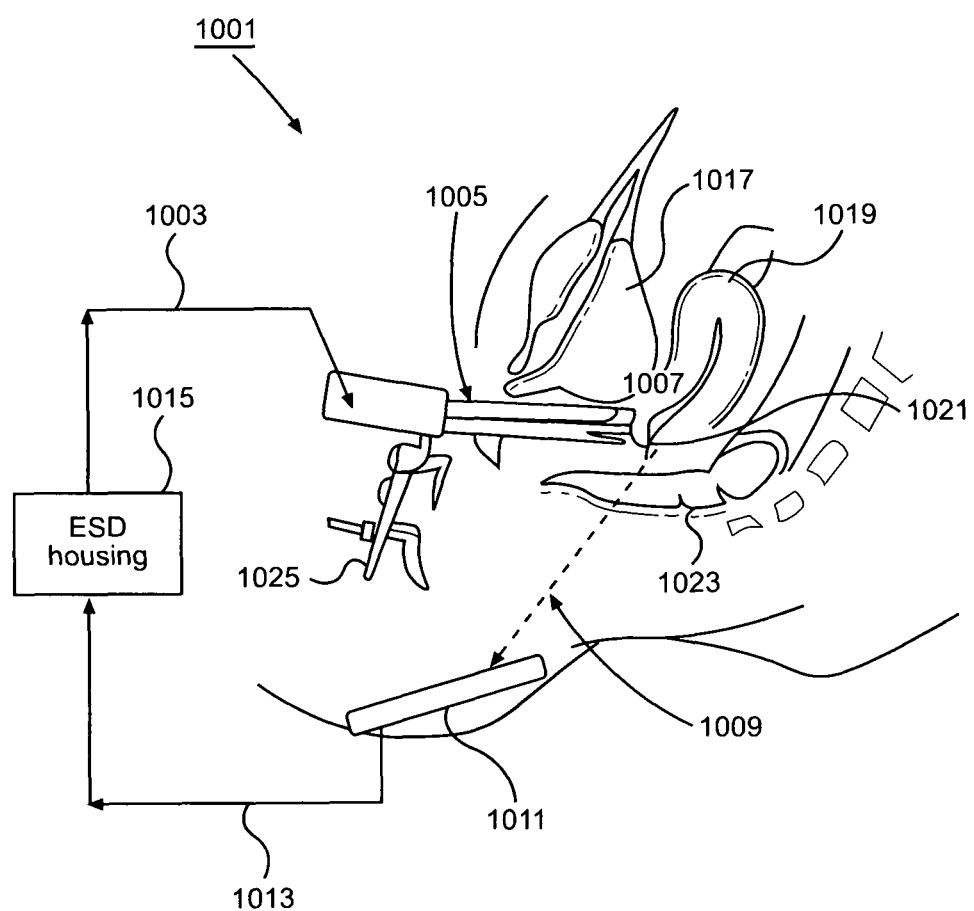
FIG. 10(B) is a more detailed illustration of the monopolar procedure with the second electrode receiving the RF signal from the first electrode tip on the ESD's probe.
Figure 11:
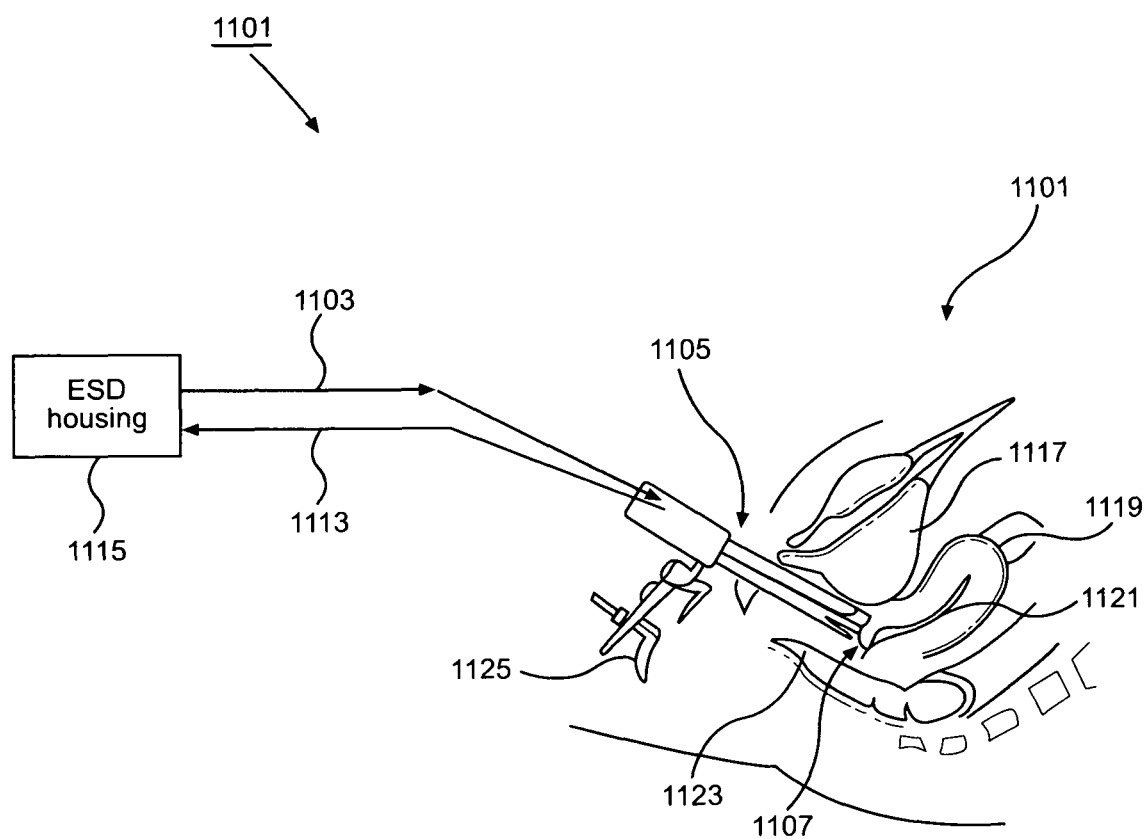
FIG. 11 illustrates an arrangement of a bipolar electrosurgical procedure where the RF signal current path runs within the probe of the ESD.

FIGS. 10(A)-(B) and 11 are next referred to in explaining use of the disclosed ESD for bipolar and monopolar radio frequency generated electrosurgical procedures. FIG. 10(A) is an illustration of an arrangement of a monopolar-electrosurgical procedure where the RF signal current path runs from one electrode at probe 1005 through the patient's body to a second electrode 1011 placed against the patient's skin for receiving the RF signal. FIG. 10(B) is a more detailed illustration of the monopolar procedure with the second electrode 1011 receiving the RF signal from probe 1005 of the ESD.

As discussed previously, one aspect of the electrosurgical treatment is the ESD's use in a bipolar procedure in which the two electrodes of the heating element are both on the distal end of the probe and applied to or near the surgical site. FIG. 11 is an illustration of an arrangement of a bipolar electrosurgical procedure where the RF signal current path runs within the probe of the ESD.

In another embodiment, there is a monopolar procedure where only one electrode is applied to or near the target tissue at the surgery site, and the second electrode is in the form of a ground pad that is positioned on the patient's body remote from the surgery site. FIGS. 10(A)-(B) illustrate a monopolar surgery procedure.

Referring first to the monopolar electrosurgical procedure arrangement 1001 of FIGS. 10(A)-(B), and to FIG. 10(B) in particular, a probe 1005 is directed to the surgery site 1007, which in this illustration is in the patient's pelvic area. Probe 1005 is connected by conductor 1003 to the ESD housing 1015. A conductive pad 1011, referred to at times as a ground pad, is attached to another part of the patient's body, in this illustration being on the patient's buttocks (FIG. 10(A)). Conductive pad 1011 is connected by conductor 1013 to ESD housing 1015, which completes the current loop from the signal generator in ESD housing 1015 through probe 1005, through surgical tissue at site 1007, through ground pad 1011 and back to ESD housing 1015. Note that in this loop, the current is transferred through the patient's body along dashed line 1009 to the second electrode which is ground pad 1011.

Referring next to the bipolar arrangement 1101 of FIG. 11, the arrangement is similar in some respects to that of FIGS. 10(A)-(B) in that the housing 1115 connects to a pair of conductors 1103, 1113 and a probe 1105, which 11110511 has its distal end directed to the surgery site 1107 (also depicted in this illustration as being in the patient's pelvic area). Differently here, both electrodes are contained in the probe tip area, such as at both ends of a heating element, so the current flows into the probe and flows out of the probe back to ESD housing 1115. The second electrode is not remote from the surgery site and no current passes through the patient's body, except for the current that passes through the tissue to be targeted during the electrosurgical procedure.

In one embodiment, the change of heating element involves a change in the waveform signal delivered from the ESD housing to the probe. Waveform generation is performed by AC drive signal selection controls 105. This component is coupled in particular with AC signal switching/waveform generating controls 127 in carrying out functions of activating a certain waveform based on the user's selection of heating element, conducting other calculations and signal generation. AC signal switching/waveform generating controls 127 and AC drive signal selection controls 105 are also coupled to signal generator modules shown in FIG. 3 to carry out the controller functions. The signal generator modules include microwave signal generator 307, radio frequency signal generator 318, laser signal generator 317 and ultrasound signal generator 321 in FIG. 3.

Electrical characteristics of a number of AC signal heating elements are identified and stored in controller 107, in which the AC signal heating elements have their designated electrical characteristics already programmed in so that when a particular AC signal heating element is selected, its power, frequency, and waveform are predetermined according to the optimal characteristics recommended for that particular AC signal heating element. In other embodiments, variations are recommended for certain surgical procedures and environmental conditions of the surgery. These variations may be displayed, such as having been downloaded, according to manufacture or standards recommendations. In another embodiment, the electrical characteristics are automatically populated into the drop-down list, or other information table, for each variation. In another embodiment, the user inputs desired settings using operator input panel 111, such as for power, voltage and current, or designating values as being AC or DC. Then when stored variations of, for example, laser heating elements are presented and a particular one is selected, the operating parameters for that selection are already stored, and the heating element automatically operates using those parameters, such as a certain power output at a certain sine-wave frequency.

Often in electrosurgical procedures, a continuous AC signal is not desirable due to overheating, which may adversely affect both the equipment and the patient. In addition, the AC signal could cause electrical noise interference with other medical devices. Alternative embodiments or options in the generation of an alternating signal include a rectified AC signal, a pulsed either AC or DC signal, a clipped AC signal and an AC or DC signal with a duty cycle that may be variable by the user. With these options, the user can more precisely control the heating, the safety of the patient is enhanced, and the precision of the surgical process is improved.

Signal characteristics capable of being modified are projected on display 109 in response to a user selecting a specific heating element and activating a switch to have this information retrieved from memory and made viewable on display 109. In various embodiments, the characteristics may include available waveforms, duty cycles and the other signal parameter variations available.

While signals herein are at times referred to as AC signals, it is to be understood that this includes, for simplifying this discussion, pulsed DC signals, rectified signals and other waveform-shaped signals as well, even though they technically may not be alternating in terms of their polarity.

In another embodiment, the user's selection of available choices is performed using a touch screen for display 109 or using a mouse connected to USB input 115. Display 109 may also display additional information as described in this disclosure, including images, video, web sites, user input, and so forth. In yet another embodiment, a customized selection is made whereby the user, for example, may select a non-listed power output, such as a low 500 mW output perhaps due to the tissue condition being targeted. In this case, the user selects a user-input for power and, and enters the 500 mW in operator input panel 111. Controller 107 calculates the other electrical parameters, such as current, voltage or/and impedance, for this 500 mW output and if this adjustment is within the performance capability of the controller with the laser heating element now connected to the device, a confirmation of the change to the customized selection is presented on the display and the user is ready to proceed with the procedure using the inputted or selected parameter value. If the adjustment is not within the performance capability of the controller with the laser heating element now connected to the device, an indication to that effect, such as "not available" is displayed on display 109.

In another embodiment, the reference to the customized selection being within the performance capability of the controller is meant that the controller has a finite range of variables either downloaded or manually inputted via a keyboard connected to USB input 115, or a similar input that is incorporated in, or provided as an external input on, USB input 115. This data in particular takes into account the manufacturer's specifications and information associated with the particular model heating element or heating element/probe tip combination to determine the range of operating values for that particular heating element device.

In another example, AC signal switching/waveform generating controls 127 is included within, and as part of, controller 107, even though it is not limited in this way. AC signal switching/waveform generating controls 127 optionally is an external component connected to controller 107, in which case controller 107 delivers the operating voltage and current beyond the controller to AC signal switching/waveform generating controls 127.

If a heating element is found to have specifications that require a DC signal or both DC and AC signals, then optionally a connection is made with DC current path 123 to provide the DC signal.

By way of example, a procedural guide or checklist is projected on display 109 for the selected laser heating element. Double clicking on the selected laser heating element, or use of another switching mechanism, will present options available for the laser heating element, such as a lower power or a higher power option for laser heating element. If, for example, a laser heating element is being used and more technical information is needed there on-site, the operator uses either or both of (1) memory 108 and pulls up material stored therein or (2) uses Ethernet input 117 to connect to a particular web site to access the desired information.

If the user wishes to change an operating parameter, such as to set the laser heating element at a customized power level, the user inputs data using operator input panel 111 and proceeds as described with reference to changing an operating parameter for the laser heating element. The display has a device on/off switch associated with the display or positioned elsewhere on the device.

Ceramic Ultrasonic Heating Element

In another example or embodiment, ceramic piezoelectric elements are used for heating elements that generate heat using ultrasonic energy. Such ceramic heating elements function based on their size, typically being circular with an approximate 3.2 mm diameter and 0.19 mm thickness. As with resistor heaters, ceramic heaters are made up of one or multiple ceramic elements. For example, an effective ceramic element for this purpose is made of micromachined lead zirconate titanate (PZT) due to its favorable piezoelectric properties and electromechanical coupling. PZT converts electrical energy to mechanical vibrations based on the ultrasound drive signal frequency and amplitude. The ultrasound mechanism is based upon a direct absorption of the ultrasound energy within a dissipative medium.

PZT is an example of the use of a material in combination with a technology, such as ultrasound in this instance, to generate heat for use in an ESD. A characteristic of PZT is that the temperature of the piezoelectric PZT element increases while the ultrasonic drive signal converts the electrical energy to mechanical energy. The PZT element will be used by way of example in this discussion. As an example of a PZT ceramic element's operating conditions, a PZT achieves a maximum temperature of 120° C. at 160 mW input power, and, at an interface temperature of ~150° C., a PZT ceramic ultrasound heater probe brands animal tissue in 2-3 seconds with a 10 VRMS drive voltage.

Figure 12:
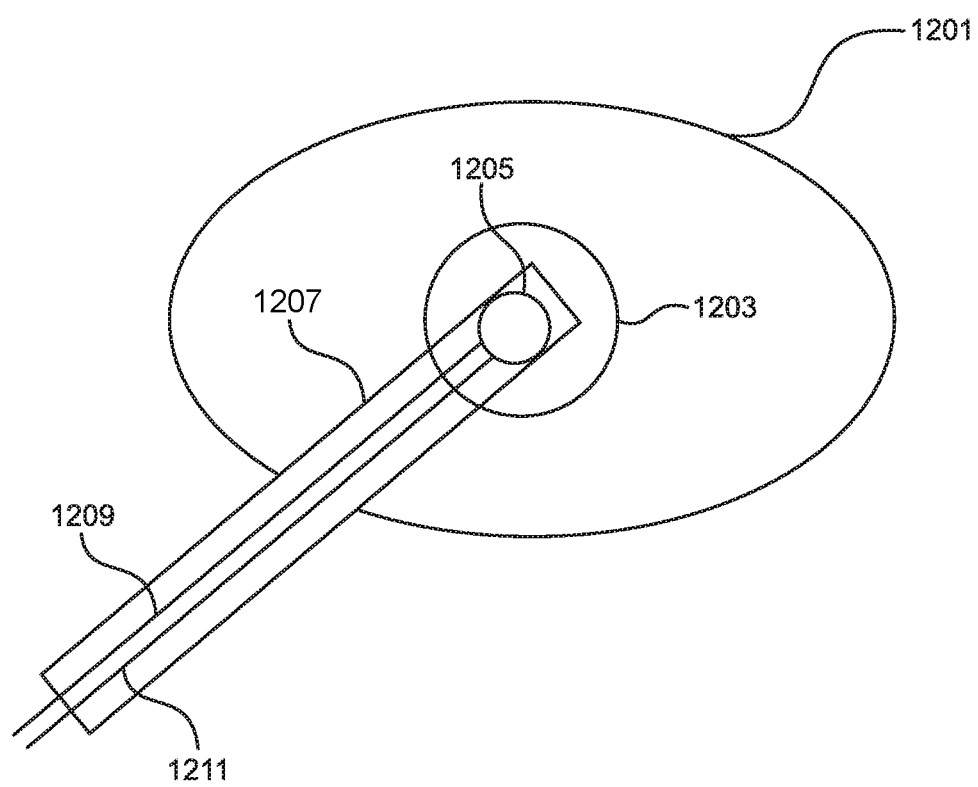
FIG. 12 is a conceptual illustration of the use of an ultrasound ceramic disk heating element.

FIG. 12 illustrates the concept of destroying or cauterizing a targeted tissue 1203 located within surrounding tissue 1201 by use of a cauterization probe 1207. At the distal end of the probe 1207 which comes into contact with the targeted tissue 1203 is the PZT 1205, which is connected to two leads 1209, 1211 through which the driving ultrasound signal is transmitted from the controller of the ESD to the tip end of the probe 1207.

Ceramic with PZT Material

As discussed previously above and in one embodiment, a ceramic ultrasound heating element is made of a PZT material. Heat generated in a ceramic ultrasound PZT heating element is a function of different element geometries, operating frequency and drive voltage. The temperature of the PZT actuator is a function of the electric field applied across its electrodes. Hence, for a given voltage, higher temperature is achievable by reducing the thickness of the ceramic element because, and likewise, for a given ceramic element, higher temperatures are achievable by increasing the drive voltage across the electrodes.

Hence, when using a ceramic ultrasound heating element in the disclosed ESD, the operator can control and vary the heat generated during a procedure by varying the operating frequency or the drive voltage for a given ceramic element. While operating parameters vary, some typical figures are the following: dimensions for a circular PZT ceramic heater are a diameter of 3.2 mm, a thickness of 0.19 mm, and a radius of 10 cm; sinusoidal waveform actuation voltage with a peak-to-peak amplitude of 4 to 6 volts and an actuation frequency of 4 MHz; and reaching a temperature of 120° C. using 160 mW input power.

Smoke Evacuator System

A byproduct of the various forms of electrosurgical medical care is the generation of smoke/fumes which may contain human papillomavirus (HPV) particles that may be transmitted to the operator who breaths in or comes into contact with the smoke/fumes. In addition to HPV particles, other viral DNA, bacteria, carcinogens, and irritants are also known to be present in electrosurgical smoke.

Figure 13:
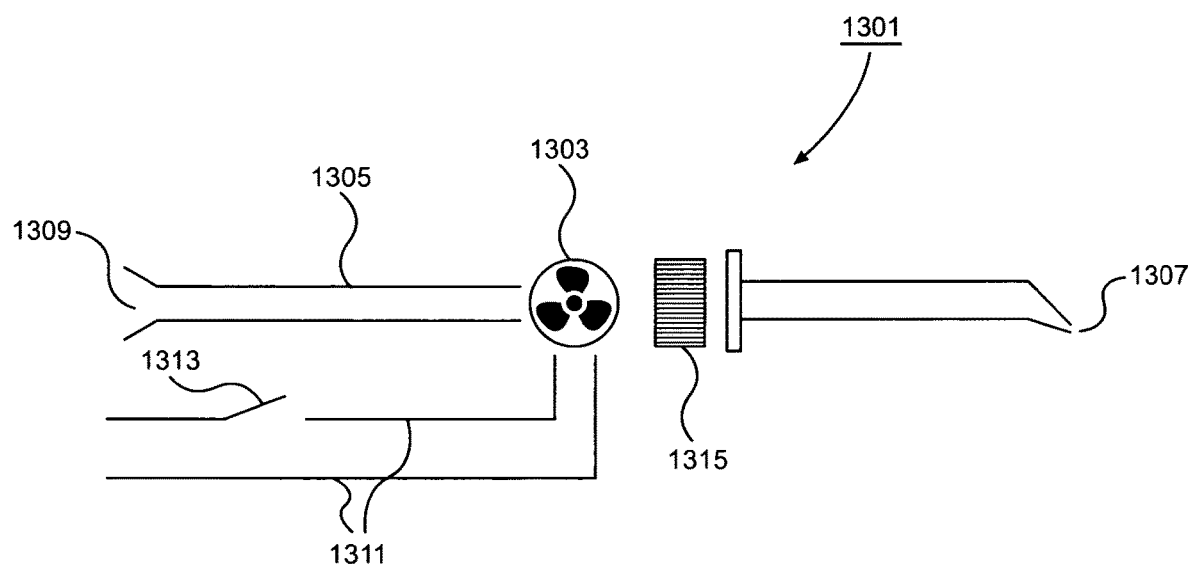
FIG. 13 illustrates the smoke evacuator system as used in the disclosed ESD.

FIG. 13 illustrates smoke evacuator system 1301 that is a part of the disclosed ESD. Smoke evacuator system 1301 includes a suction fan 1303 inline with an evacuation conduit 1305. The evacuation conduit 1305 is made from a choice of materials as a matter of design choice, so long at the material is compatible with the operating temperature of the smoke evacuator system 1301, namely, the temperature of the evacuating air and especially the operating temperature at the area of the probe tip.

At one end referred to as the intake end 1307 of the evacuation conduit 1305 is an intake nozzle that extends to the probe tip area. When using the smoke evacuation feature, that is, when suction fan 1303 is activated, the intake nozzle is positioned, for example, about 2-5 cm from the operative site and sucks in any smoke and other byproduct produced as the discharge end 1309 of evacuation conduit 1305 is positioned so as to discharge the sucked-in air from the surgical area safely to the outside. The exact position of discharge end 1309 is a matter of choice. As one example, discharge end 1309 is located near the connection of the detachable probe to the ESD housing. A filter 1315 is placed in-line with the fluid (includes air) flow in the evacuation conduit 1305. While usable filters come with a wide range of filtering capability, a filter envisioned for use in this application is capable of filtering down to sub-viral sizes of around 0.1 micron.

The online fan has conductors 1311 connected through an on/off switch 1313 to the power supply to activate the fan. In one embodiment, the smoke evacuator system 1301 is automated whereby the fan 1303 is turned on concurrent with the turning on of current flow through the heating element of the probe tip. In another embodiment, the smoke evacuator system 1301 can be set, such as by means of a "manual-auto" fan switch on the ESD, so that the fan 1303 is manually activated by the operator using a switch. This manual mode may be used to reduce power consumption and to use the fan 1303 only when the operator observes smoke at the surgery site.

In connection with the replacement of probes, the smoke evacuator system 1301 can be built attached to each probe type, or more economically, the smoke evacuator system 1301 can be a detachable unit that can be detached and re-attached to the newly connected probe.

Field Programmable Gate Array

In one embodiment, a field programmable gate array (FPGA) is operationally connected to the controller and to the heating element of the probe tip to allow the operator to custom set a desired choice of parameter for the ESD's operation at the probe tip.

For clarification as regards terminology, a probe tip may or may not have a discrete heating element. The target tissue has a resistance of its own that may suffice for the needed resistance to carry out the surgical procedure at a certain power level, current flow or voltage setting, as examples. Therefore, as used herein, it is understood that a probe tip may include a resistance or impedance value associated with the probe tip, with the resistance being dependant of factors such as the probe tip's dimensions and structure. In addition, the resistance of the target tissue is added to any other inline resistance to give a total resistance at the probe tip and its immediate area, for purposes of calculating other electrical parameters, such as power, voltage or current. Likewise, reference to a discrete resistor heating element is understood to also include the resistance of the probe and the target tissue if the total resistance is to be determined. "Probe" includes the probe tip and the heating element used to generate heat at the probe tip, be it radio frequency waves, microwave, laser or ultrasound vibration, as possible examples.

When a type is selected, such as radio frequency (RF), information is projected on the display, such as in a drop-down file or a table, regarding parameter settings and choices available for modifying those settings in using the RF probe. In one embodiment, the initial setting shows the signal sent to the probe tip as being a sine wave at 350 KHz and shows other optional operating frequencies. In another embodiment, the initial power setting shows 10 watts of power at the probe tip, based on a certain resistance, and with it other alternative operating power levels. The user either accepts the default settings or switches to any of the alternative settings for any one or more other parameters. In one embodiment, with a touch screen display, the choice of settings is selected by touching the screen at the proper spot. In another embodiment, the choice of settings is selected using other known types of switches positioned on the ESD, such as rotary switches or an array of membrane switches.

With a FPGA, in another embodiment, the user configures the heating element at the probe tip, by setting or programming logic blocks or gates and RAM block to achieve, for example, a certain resistance at the probe tip, or set a parameter such as set for a constant power operation in which the voltage may vary to maintain the constant power. Additionally, the current parameter is set in the same manner. Digital computations can thus be realized by using FPGA component adjustments accordingly. In another embodiment, the embedded microprocessor(s) of the FPGA form necessary settings for a particular probe type that is attached to, and operates as part of, the ESD. For example, a switch on the ESD gives the user the option of selecting a certain type of probe and/or a certain type of heating element.

The FPGA has the ability to be programmable which allows the FPGA to refigure itself to suit the separate attachable probe that is connected to the ESD box. For example, if the user indicates that the connected probe is an ultrasonic vibration electrosurgical probe, the associated frequency is generated in the controller, for example, and the default or selected parameter settings (power, voltage, current, wavetype, timer) are produced by the FPGA. In one embodiment, FPGA is included as part of the controller or, in an alternative embodiment, it is operationally connected to the controller but separate from it. In another embodiment, calculations relating to the electrical operating parameters for any one type of probe are determined at the FPGA or at the controller. The FPGA allows the user to make changes, make selections, emulate hardware, re-program and fix bugs, and solve any problem that is computable, there on the spot, in-the-field.

Auto-Sterilization

Another feature of the disclosed ESD is its auto-cycle sterilization capability. Since many organisms (virus, bacteria, etc.) are deactivated by heat above 100° C., an automatic feature uses an activation button to auto-cycle the probe tip to 134° C. to sterilize the tip. The 134° C. is a preferred temperature for sterilization. This temperature is not stringent, and any suitable temperature to accomplish the sterilization can be used. This built-in sterilization feature saves time, protects the patient and allows for meeting advisable surgical standards. In addition, sterilization of the probe shaft can be performed by wiping down the shaft with an antiseptic, soaking it in a sterilization fluid, by steam autoclave or chemical disinfecting. Alternatively, a disposable, sterile sheath is placed over the probe shaft and discarded between patient uses. In another embodiment, the sheath is made out of a material that provides the fiber optic lighting transparency and diffusion so as not to impair the probe-length lighting feature as discussed above. In yet another embodiment, the probe itself is molded with a material that withstands heat autoclave temperatures and a high humidity.

Membrane Switch Array with LED Indicators Along the Probe Length

LED lights provided at the instrument tip illuminate the surgical area. The transmission path within the probe shaft is a fiber optics cable for transmitting light from a light generating source. Alternatively conducting wires are used to carry electrical signals to activate a plurality of light generating sources positioned at the tip end to illuminate the surgical area.

Figure 14:
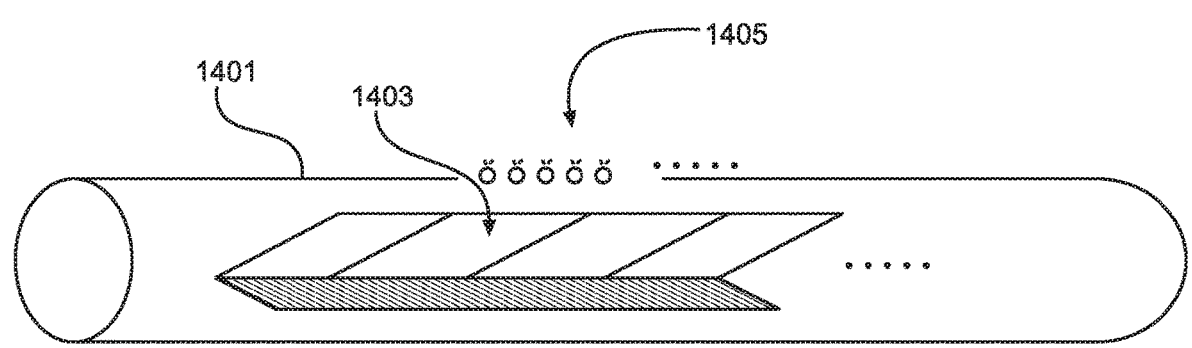
FIG. 14 shows a segment of a straight tubular probe sheath with an illustration of membrane switches and LED indicators mounted thereon.

FIG. 14 shows one embodiment of a probe 1401, or alternatively a sheath that is fitted over probe 1401, with a linear array of membrane switches 1403 and a strip of visual indicators 1405. This provides convenient function switch controls to the operator and light indicators for various operational conditions for easy viewing by the operator. The probe shaft is formed of a light transparency material, such as plastic, and is coated with a light diffusing material, such as a light diffusing coating. In one embodiment, visual indicators 1405 are LEDs but alternatively there are other indicator types including color indicators.

A membrane switch is characterized by having a flexible substrate that provides a flat or contoured surface, similar to that of a touch screen. When used on the ESD, of membrane switches provide a smooth, sealed outer surface and a switch interface that allows for communicating commands, in the midst of an operation for example, to the ESD and to the controller in particular. However, the switches of the ESD are not limited to membrane switches and can be any type of switch.

The switches can be used for any function of the ESD, and in one embodiment are connected for functions that are most used during a surgical procedure so to provide convenience and effectiveness in activating optimal conditions during steps in the surgery. For example, in one embodiment, a switch is connected to a temperature adjustment of the heating element, such as with "+" and "−" indicators. With a proper positioning of the switch on the probe, in another embodiment, the operator uses the thumb to toggle or activate the two switches to increase or lower the temperature of the heating element during a procedure.

FIGS. 15(A)-(E) present FIG. different types of membrane switches, some with LED light indicators, as examples to illustrate the possibilities of the design arrangement of membrane switches 1403 and visual indicators 1405. The switch types also apply to the switches discussed later with respect to FIGS. 19(A)-(B). The different array styles, presented as examples, make the membrane switch easily accessible and visible to the user during a surgical procedure. FIG. 15(A) shows two linear rows of membrane switches, each with an LED light indicator positioned above each switch. FIG. 15(B) shows a keypad arrangement of membrane switches 1-8, each with an LED light indicator positioned above each switch. FIGS. 15(C)-(E) show other various types and arrangements of membrane switches. The respective LED lights indicate when a particular switch is activated. The switches mounted on the probe provide a smooth surface aligned with that of the probe so there is no obstruction created by the switches mounted on the ESD and within finger control of the user.

In one embodiment, the LEDs are used as indicators for various states, statuses and conditions of operation of the ESD. They can be contained in the linear membrane material. In one embodiment, the membrane switches are positioned side by side to make it convenient for thumb activation by the clinician during operation of the ESD. In another embodiment, the LEDs are arranged in a linear array, such as of 4-5 LEDs that show, for example, the percentage of time the procedure is completed in the operation. In various other embodiments, other LEDs display the battery life, such as yellow for when the battery power is getting low and a blinking yellow for when the battery needs to be recharged before starting another procedure. Features as previously described of the controller make these features simple to program and flexible for variations, etc.

The emitted light from the LEDs is directed toward the probe material so that the light is directed to the outside, surrounding area of the probe. A light diffusing coating is applied on, for example, clear plastic material of the probe's outer body (probe shaft) to emit light throughout the length of the probe. A preferred application of light diffusing coating is between 0.5 and 1.0 mm in thickness. One such coating material produced by DuPont™ is known as WhiteOptics®, as one of a number of DuPont diffuse light optical materials. Another example is the Guangzhou light diffuser coating, available from Guangdong Guoweixing Plastic Technology Co., Ltd. Guangdong, China.

Thus, LED lighting can be supplied from both the instrument tip and along the length of the probe to provide lighting and visibility during the surgical process. This is especially important in giving visibility to the vaginal vault during the procedure without the cumbersomeness of adding lighting into a closely enclosed area. The fiber optics sheath in combination with the light-diffusing coating dramatically enhances the lighting beyond just the tip of the probe.

An alternative option is to apply a sheath over the probe whereby the sheath has strips of LED lights affixed on the inside of the sheath with the lights directed outwardly from the sheath. This alternative option allows for the lengthwise lighting for the probe to be added onto a probe that was not manufactured with the lengthwise lighting already inside and running at least a part of the length of the probe.

Cool Down System and Cool Down Mode Option

Figure 16:
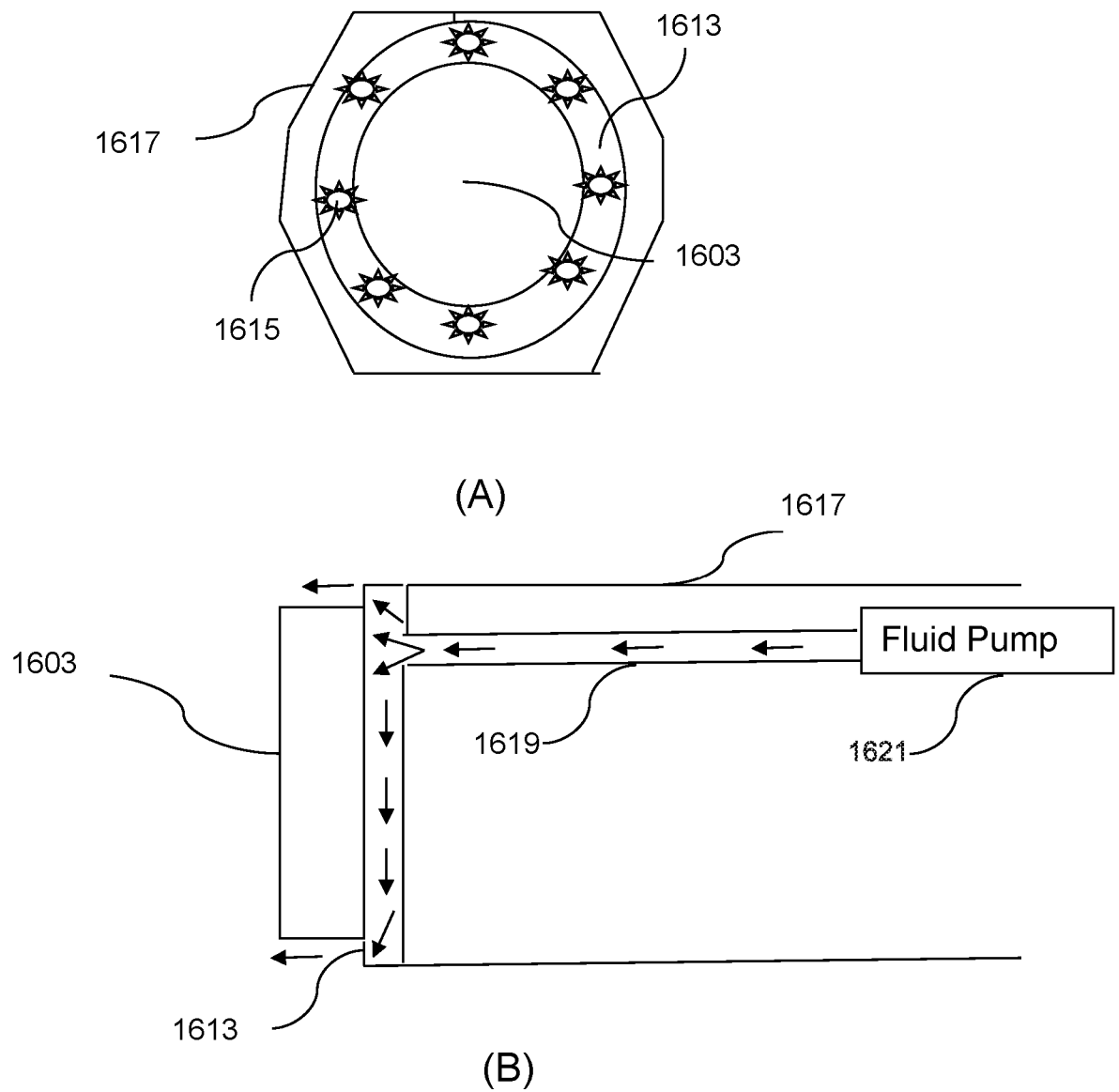
FIG. 16(A) is a frontal view looking at the heating tip of the probe with a circular ring of cooling fluid apertures surrounding the heating tip.
FIG. 16(B) is an illustration of operation of the fluid cooling system inside an ESD probe.

FIGS. 16(A)-(B) illustrate the concept of the cooling-down feature of the disclosed ESD and its probe tip design.

A problem with known types of electrosurgical probe tips is the sticking of human tissue to the tip which becomes problematic when the probe is to be removed from the tissue area after the surgical procedure has been completed. The disclosed ESD overcomes this problem by providing a cool down mode for the probe tip for cooling off the probe tip to prevent sticking of tissue and/or other foreign matter to the probe tip when the probe tip is sought to be removed from the patient's cervix, or other surgical area of the body.

The cooling down is accomplished by providing an opening down the length of the probe shaft in which a small pump is positioned to produce cool fluid (from outside the patient) to cool down the tip 1603 after the procedure. FIG. 16(A) is a top view looking down on the tip 1603. The tip 1603 includes a circular rim section 1613 that extends circularly outward from the circular tip 1603, and apertures 1615 located in circular rim section 1613 for passing a cooling fluid there through to cool down tip 1603. The tip 1603, circular rim section 1613 and apertures 1615 are located at the distal end of the probe structure 1617, which may be a straight or angled hand-held probe or may consist of a probe with an angled handle for grasping the probe. Fluid flow is activated by fluid pump 1621 (FIG. 16(B)) and passes through apertures 1615 to cool down the tip 1603 at the conclusion of a surgical procedure to reduce, minimize or eliminate a sticking or adhering of bodily tissue to the tip 1603 or burning of vaginal wall tissue while removing the probe if it accidentally touches the vaginal wall. While eight apertures are shown in FIG. 16(A), the number and positioning of the apertures are matters of design choice. Each aperture receives a conduit that directs the fluid flow into and out of the apertures to have cooling fluid surround tip 1603.

FIG. 16(B) is an illustration of a side view of FIG. 16(A) to show fluid pump 1621 and fluid flow. Fluid pump 1621 is activated by an on/off switch (not shown) and an electrical connection (not shown) to cause fluid from outside, that is, from outside a body cavity if the surgical procedure is within the body cavity, to flow through a conduit 1619 to the tip 1603. The fluid passes through conduit 1619, is routed to circular rim section 1613 flows through the apertures formed in circular rim section 1613 and is directed to flow around the tip 1603.

Another alternative structure and method for cool down is to provide a Peltier cooler, also known as a thermoelectric heat pump, at the tip 1603 that is activated at the housing to cool down the tip 1603. The Peltier cooler is a solid-state active heat pump that transfers heat from one side of the device to the other to accomplish the cooling at the desired point, which in this instance is at the distal end of the probe to cool down the probe tip.

Anti-Stick Probe Tip

One Suitable Type of Thermal Spray Non Stick Coating is DuPont's® Teflon®

Figure 17:
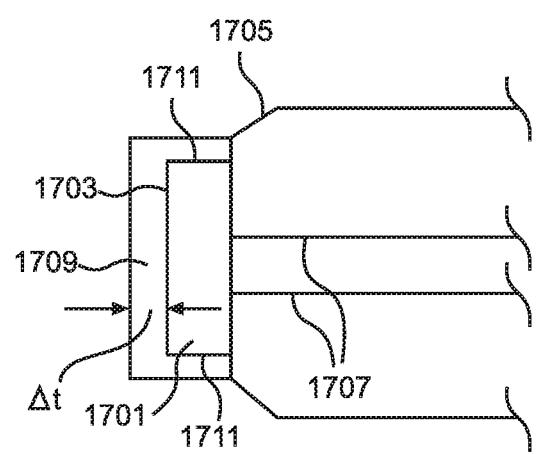
FIG. 17 is a side view of a probe tip on an end of the probe showing a probe tip with a non-stick coating applied to the probe tip.

FIG. 17 illustrates a second solution to the sticking problem: coating the probe tip with a non-stick coating material that is compatible with the tip's operating temperature. The tip is made of a material of high thermal conductivity, such as copper, aluminum, nitride, etc. so that the heat transfer from the heating element is fast and no delay in tissue temperature increase is experienced. A non-stick surface is advantageous to prevent sticking of tissue when it is ablated or heated to boil the water out of the cells and kill the cancer cells. A smooth ceramic surface may also work. The non-stick feature is applied to the tip or is inherent in the material the tip is made of. The coated or constructed tip provides a material surface that is anti-stick, especially to cervical tissue in an enhanced temperature environment. The coating material has a smooth surface to prevent the hot probe tip from sticking to the cervical or epithelium tissue upon removal of the probe. This probe coating solution can be used alone or in combination with the cooling down solution previously described, namely that of using the cooling down air flow through apertures on a rim of the probe tip.

One suitable type of non-stick coating is DuPont's® Teflon® (PTFE) Non-Stick Dry-Film Lubricant Aerosol Spray manufactured by DuPont, Inc., Wilmington, Del. This non-stick coating for high temperature applications can offer a big advantage over traditional Teflon or other release coatings. Thickness of thermal spray non-stick coatings can be as low as 0.003 to 0.005 inch or as high as 0.010 to 0.015 inch per surface and provide an extremely hard adherent bond to the probe tip base material.

FIG. 17 is a side view of a probe tip 1701 at the end of a probe sheath 1705, or if the probe has a sheath outer surface, then it would be the outer surface or end of probe sheath 1705. A pair of wires 1707 provides the transmission path for current delivered to a heating element (not shown) in the probe tip. A top surface 1703 of the probe tip is coated with a non-stick material to prevent the sticking of the probe tip to human tissue during or after the surgical procedure. The coating, such as DuPont's® non-stick dry-film lubricant aerosol spray or other non-stick coating, can be applied to the probe tip, such as by being painted on or sprayed on, can prevent potential problems to the surrounding tissue and to the patient's safety and can provide comfort when the probe is sought to be removed from the patient's surgical area.

Coating layer 1709 is applied to probe tip 1701. Note that coating layer 1709 is not drawn to scale. It is, in fact, shown much larger than the layer actually would be as a coating layer, and is enlarged to make possible the showing of the tip and its components, such as thickness Δt of coating layer 1709. Note also that the coating is applied to both the top surface 1703 of probe tip 1701, but also over the side areas 1711 of probe tip 1701. Alternatively, the coating is applied just to the top surface 1703, although it has been found that a total covering of all sides of the probe tip gives better protection against the undesired sticking of matter to the tip during or after the surgical procedure.

Method of Operating According to One Embodiment

Figure 18:
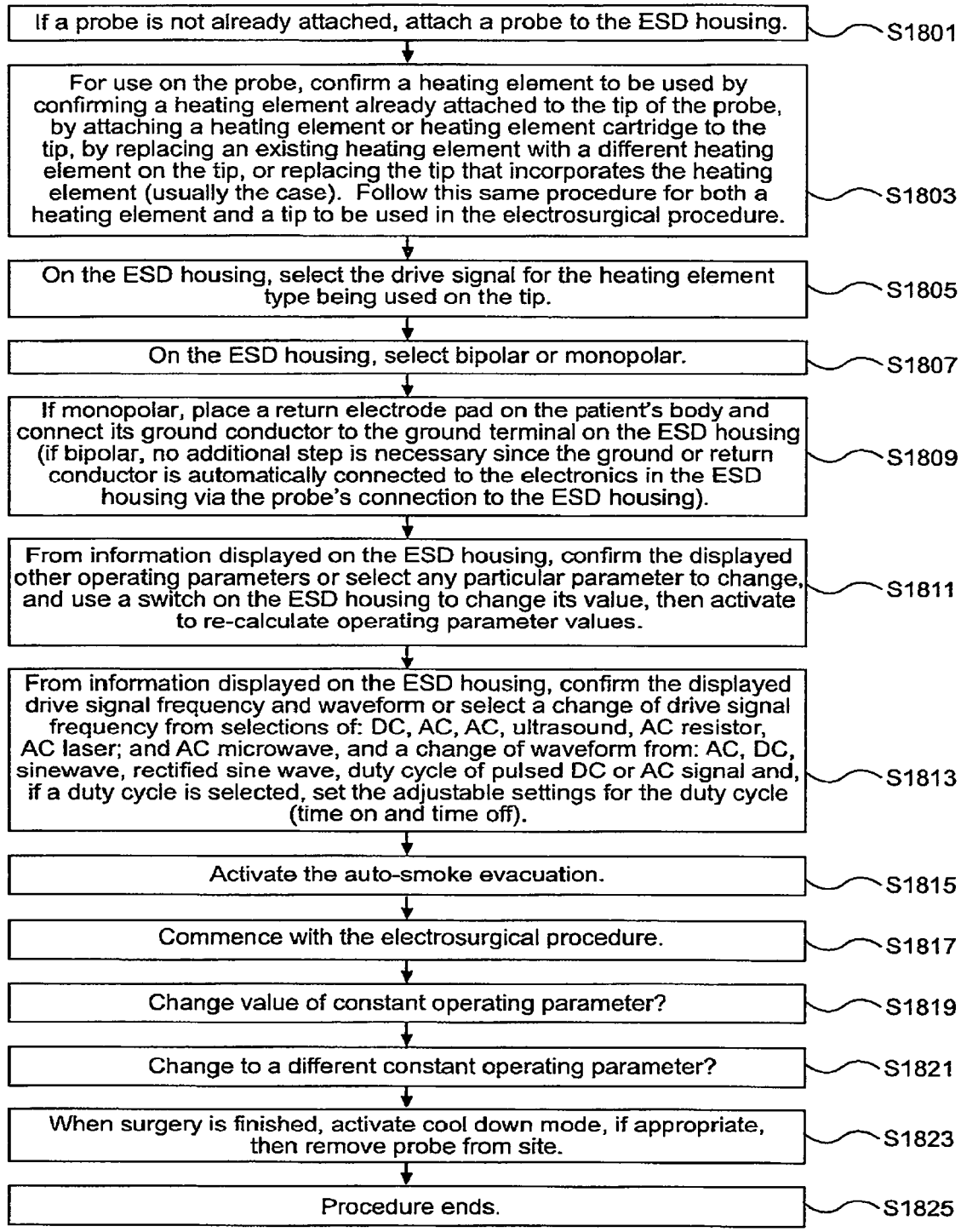
FIG. 18 is a flow chart that shows potential steps in a process of using the ESD according to this disclosure that incorporates certain of the described features.

FIG. 18 is a flow chart that presents steps in a process of using the ESD according to this disclosure that incorporates certain features in one embodiment of the disclosure. At the start, step S1801, the user either attaches a probe to the ESD housing if a probe is not already attached.

At step S1803, the user checks to make sure the desired heating element to be used in the procedure is attached to the far end of the probe, which is the end closest to the surgery site whereas the probe's opposite end is connected to the ESD housing. In one embodiment, the desired heating element may already be attached. If not, then the user attaches the desired heating element to the probe if no heating element is already attached or removes a heating element and replaces it with the desired heating element. In another embodiment, the heating element is in a cartridge form. In another embodiment, if a resistor heating element is already attached, the user uses a different resistor value in which case the resistor component is replaced with the desired resistor value. This same procedure equally applies to the probe tip as well. In another embodiment, a probe tip of a certain geometric design or shape is attached to the probe as part of the heating element and probe configuration. Some types of heating elements may not use a probe tip so, in that case, no probe tip consideration is necessary.

At step S1805, once the desired heating element and probe are attached on the probe, the heating element selector switch on the ESD housing is set to the type of heating element that will be used. In one embodiment, the selections available are: resistor, laser, microwave and ultrasound heating elements (frequency changes of the RF drive signal).

At step S1807, the user makes the setting on the panel of the ESD housing, for example, for either a bipolar or monopolar procedure, according to the heating element used. A bipolar heating element has both electrodes at the site of the surgery so to form or complete the current path that flows through the probe to and from the ESD housing. Alternatively, a monopolar heating element has a single probe at the site of the surgery, and the ground probe is connected by means of a ground plate positioned on the patient's body, so that the current path runs through the patient's body between the two electrodes. At step S1809, if a monopolar probe is being used, the user has to connect the ground conductor that runs from the ground plate back to the ESD housing. This ground conductor is connected to an input ground jack on the ESD housing.

Certain operating parameters are presented on the display based on the heating element setting. These parameters may be as examples, the drive signal's frequency, power setting and the temperature to be reached at the heating element. At step S1811, the user checks these readings and can accept them as shown, or can select any one parameter to change, such as to be made constant at a certain setting.

For example, the user may set the temperature for 112 degrees and further set that this is to be maintained constant at this temperature. This may mean that the current will vary depending on the resistance, which also may vary with the condition of the target tissue, but the temperature at which the destruction of the tissue is being conducted will be held constant at 112 degrees. Alternatively, the user allows the temperature to vary but set the parameter for a constantly maintained current value.

Figure 19A:
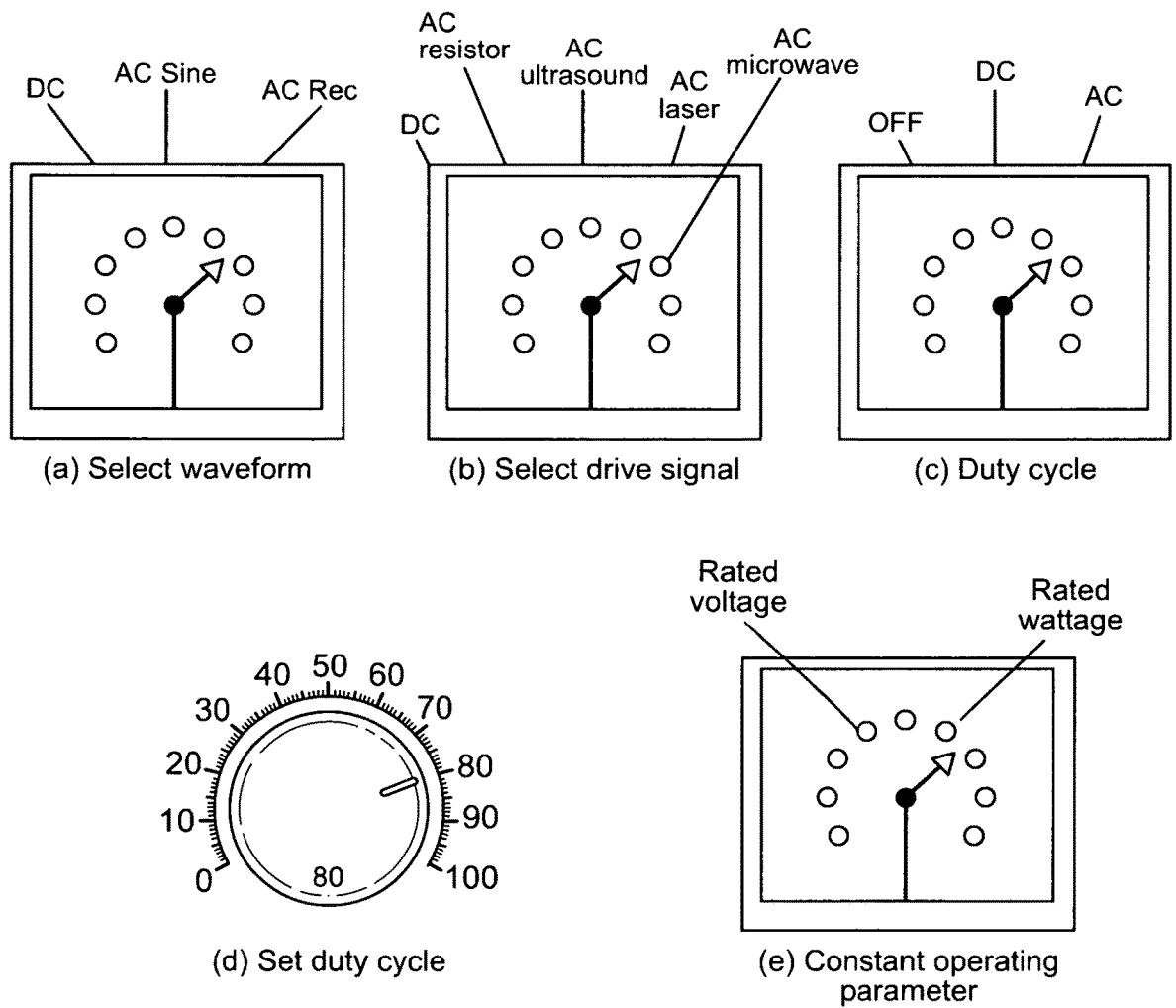

Therefore, this gives the user control over the procedure to tailor the operating parameters to suit the type of tissue and other conditions at hand so to optimize the procedure for the best results (as discussed, for example, with reference to FIGS. 18-19(A)-(B).

At step S1813, the user applies similar control over the type of drive signal to use. For example, a ready reference to a checklist stored in memory may indicate a certain frequency and duty cycle to use with the heating element chosen. At step S1813, in one embodiment, the user accepts the displayed information as to the frequency, shape and time factors of the drive signal, or, in an alternative embodiment, the user modifies any of its parameters.

The procedure is now ready to be commenced. At step S1815, the user sets the smoke evacuation feature on the probe. In one embodiment, the choices are: deactivate (the smoke evacuation feature is not active), manually activate (controlled by the user via a membrane switch controlled by the user during the surgery procedure and automatic (smoke evacuation feature is activated every time the heating element is turned ON).

At step S1817, the user commences with the electrosurgical procedure.

At step S1819, the user has the option at any time of changing the value initially set for the constant operating parameter. For example, if the initial setting was for a constant temperature of 112 degrees, and as the procedure advances the user has reason to want to reduce the temperature to 110 degrees, the user is able to reset this "constant value."

At step S1821, the user has the option at any time of changing the parameter that was initially chosen as staying constant. This might be dictated by the course of the procedure and situations encountered that might require a change in this setting. For example, if temperature was initially designated to be held constant, the user is able to now change to having a current of a certain value be the parameter to be maintained constant. This, for example, can be enacted by a "+" and "−" toggle switch or membrane switches mounted on the housing or the probe for easy finger access by the user to incrementally increase or decrease the target temperature or the target current. Details of the switch types and locations are matters of a design choice.

At step S1823, when the surgery is finished, the user can activate the feature of the disclosed ESD whereby a cool-down mode is built in whereby, in one embodiment, cooling fluid is pumped and expelled through a circular array of apertures around the probe tip. This cooling down feature allows for easier withdraw of the probe tip by reducing the adhering of human tissue to the probe tip when the probe tip is being removed from the surgical areas.

At step S1825, the user completes the procedure. At this time, the ESD can be turned off, or a new patient can be attended to, with the user starting from the top by checking the heating element on the probe and that needed for the next procedure to see if a change of the heating element is needed.

Operation of Switch Controls on the Housing

FIGS. 19(A)-(B), including FIGS. 19(a)-(k), depict various switches on the housing of the ESD according to one aspect of the first embodiment. FIGS. 19(A)-(B) are described, with some references made during the description to the flow chart of FIG. 18.

At step S1813 in FIG. 18, the user selects the waveform of the drive signal from the selections of a direct current (DC) signal, an alternating current (AC) sine wave signal, or an AC rectified sine wave signal. FIG. 19(a) is a type of switch that can be used for making this setting.

At step S1805 in FIG. 18, the user selects the drive signal for the heating element type being used on the tip from switch settings of: DC, AC resistor, AC laser, AC microwave and AC ultrasound. FIG. 19(b) is a type of switch that can be used for making this setting.

At step S1813 in FIG. 18, if a drive signal is to be changed, the user selects whether or not to apply a duty cycle to that signal. Whether setting the drive signal at the start of an initial use of the ESD, or setting it when a change in drive signal is made during the use of the ESD, FIG. 19(c) is a type of switch that can be used to set no duty cycle applied to the drive signal ("OFF") or set for a duty cycle to be applied to a DC or an AC drive signal. A duty cycle produces a pulsed DC or pulsed AC signal to the heating element. FIG. 19(d) is a type of switch that can be used for adjusting the duty cycle over the variable range for a duty cycle of from 0% to 100%.

At step S1807 in FIG. 18, the user selects either a bipolar or monopolar operation. FIG. 19(h) is a type of toggle switch that can be used for making this setting.

At step S1811 (and related steps S1819 and S1821) in FIG. 18, the user confirms the operating parameters for the procedure to be conducted and uses a switch to make any change. FIG. 19(e) is for setting the constant operating parameter and is used to explain more particularly the operating parameter setting. FIG. 7(B) shows typical rated voltage and rated wattage values for the ESD. The user selects the constant parameter, either a constant voltage or a constant power or wattage using FIG. 19(e).

If the user sets the switch for a constant voltage, the user then uses FIG. 19(f) to select the rated voltage that is to be held constant at the heating element at the selected voltage value. FIG. 19(f) is set for discrete values of 8, 10, 12, 15, 18, 20 and 33 volts, being consistent with the voltage values of 10, 12, 15, 18 and 20 volts shown in FIG. 7(B).

If the user sets the switch for a constant wattage, the user then uses a switch as shown in FIG. 19(g) to select the rated wattage or power that is to be held constant at being dissipated in the heating element during the procedure. The switch of FIG. 19(g) is set for discrete values of 20, 30, 40, 50, 60, 70 and 80 watts, being consistent with the same wattage values shown in FIG. 7(B).

At step S1815 in FIG. 18, the user selects whether to activate the auto-smoke evacuation.

FIG. 19(i) is a type of toggle switch that can be used for making this setting. By "auto-activation" is meant that a fluid gas sensor, for detecting smoke or a condition of the air in the vicinity of the surgical site, is attached at the distal end of the probe. When a fluid is detected above a pre-determined threshold level, the smoke activation exhaust system is automatically turned on to excise such detected fluids from the surgical area. As another option, a membrane switch on the ESD could activate the smoke evacuation and could be, controlled by the user's finger on the switch during the course of a treatment procedure.

At step S1823 in FIG. 18, the user can activate the cool down mode when the surgery is finished. FIG. 19(j) is a type of toggle switch that can be used for turning ON the cool down mode. Then, the procedure ends at step S1825.

Membrane Switches

FIGS. 19(A)-(B), including FIGS. 19(a)-(k), contain illustrations of various switches using the electronic switch symbols in FIGS. 19(a)-(c), (e)-(j). FIG. 19(d) uses a continuous switch ranging from 0 to 100 to indicate the duty cycle range that can be set with this switch. FIG. 19(k) is an example of a two-column array of membrane switches, as a further example of those shown in FIG. 15. While membrane switches are envisioned for use in the described ESDs, other types of switches can be used just as well, such as rotary, toggle, pushbutton, joystick, and the like.

A membrane switch is a pressure sensitive device created by the printing, cutting and laminating of precision thin film plastic materials. It provides an electrical switch made of a flexible substrate layer and a printed circuit layer, using a scheme known as print enhancement technology (PET). The switch is sometimes considered as a category of touch screens since it is activated with finger pressure on the top substrate layer, and tactile feedback can be provided with membrane switches. The switches are arranged as surface mounted keys. Classic applications of membrane switches are front panels of microwave ovens, touch screens, keyboards, remote controls and mobile devices.

The switch can be backlighted using light emitting diodes (LEDs) or optical fiber tubes, as examples. Either backlighting or side light panels can display switch settings, such as those illustrated in the switch symbols used in FIGS. 19(A)-(B). Hence membrane switches provide a desirable, low profile or, compact switch for the described types of ESD portable equipment.

FIG. 19(k) illustrates an example of a compact array of membrane switches, here having ten (10) switches in two columns in a small size, particularly suitable for the portable ESDs described. Membrane switches are characterized by having a sleek, low profile that makes their height even with a surface on which the array might be mounted. Also, see FIGS. 15(A)-(E), which show types of membrane switches including ones with light indicators. One aspect of a membrane switch is that it can operate with software and have a small display mounted next to the switch, or mounted as part of the switch, that advances a visual display as the switch advances through its settings. This type of switch is also compatible and usable with the ESDs described in the first and second embodiments.

Membrane switches in particular can be used on the handle as shown in FIG. 14 and on the panel of the housing. This includes membrane and other switches that use software with a visual display of the status of the switch. Also, the setting of the switches in terms of numbers or values used, such as constant voltage values of 8, 10 etc. or constant voltage values of 20, 30 etc., and the number of discrete switch steps, whether it is a 5-position or 7-position switch as an example, are illustrative. Membrane switches can be used to set or adjust any number of operating parameters of the ESD, including settings, treatment times or durations, activation or deactivation of various components, and the like. The number of switch steps, the parameters chosen and parameter values associated with those steps may be varied in accordance with the parameters chosen and values designed to be available to the user, and in accordance with the spirit of the disclosure.

Second Embodiment

In a second embodiment, the design of a structure for an electrosurgical device (ESD) focuses on its use in underdeveloped countries where the conveniences of a hospital, medical clinic or even a doctor's office is not available. Treatment is provided by going out to sometimes remote locations in villages to provide the needed medical treatment using the ESD on-site, such as at the housing of the patient.

For the most part, current ESDs lack the technology required for such an application. This is because of one or more of the following traits: the ESDs are costly, heavy and bulky, and, thus, unsuitable for travel to distant sites; they are complex in their design and use; and they require a reliable grid power source. A lightweight, durable, simple to use and completely portable ESD is essential for the described type of environmental encounters. The device should be usable where a power grid is not available and must be economical in cost, small and compact in size, and not bulky, for ease of carrying during travel. At the same time, operation of the ESD should be safe to the patient (such as safeguarding against excessive or high temperature) and be efficient and medically effective in its use.

This second embodiment is an electrosurgical device suitable to use in bringing treatment to those who have a preventable disease in under developed countries and to improve the lacking technology in developed countries.

An ESD is described that is specific for performing thermal coagulation for use in attacking cervical cancer in females and, particularly, cervical cancer in resource-limited settings. Thermal coagulation is an ablative therapy that utilizes a heated probe to locally destroy pre-cancerous tissues at depths up to 7 mm.

The duration for conducting the thermal coagulation procedure with the described ESD is approximately one minute or less for applying the probe tip to the targeted tissue and destroying the tissue. The contact is not necessarily continuous and may be a discontinuous contact within that one minute time period. Twenty to thirty, one-minute treatments can be administered on a single charge. The portable unit can be made compact enough to be hand-held by the user for ease of use and practicality.

Generally no anesthesia or analgesia needs to be administered to the patient. Plus, with the described ESD, assessments of results show there is no effect on fertility or pre-term labor to the patient. A simple screening examination with visual acetic acid (VIA) and treatment provided immediately to those with pre-cancerous lesions will often eradicate the cancer for their lifetime.

Second Embodiment Detail and Description with Reference to Figures

Figure 20:
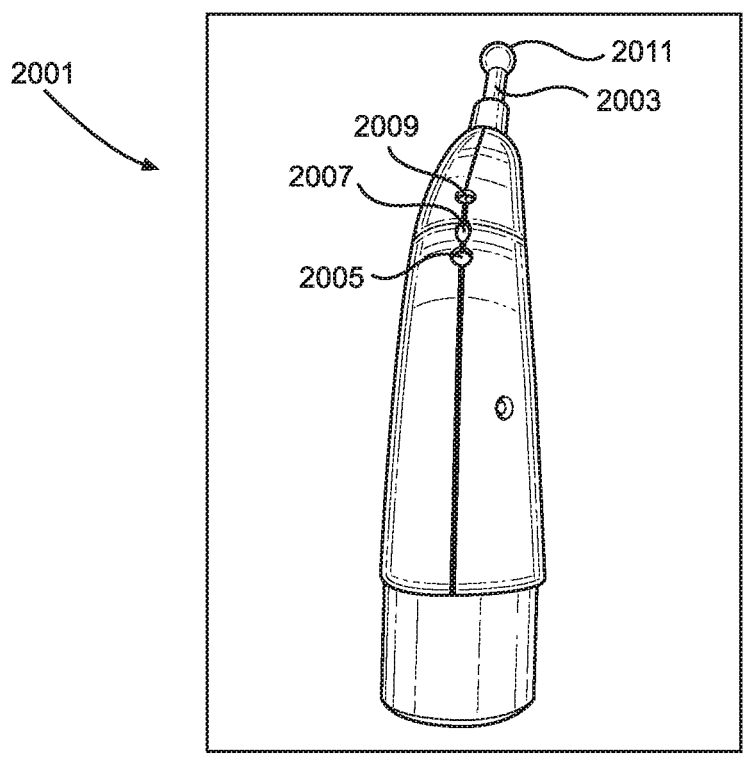
FIG. 20 is a front perspective view of a portable hand-held ESD according to another embodiment.

FIG. 20 is a front perspective view of a portable ESD according to the disclosed ESD of the second embodiment. The ESD has no connector extending from it. The ESD is completely portable with rechargeable batteries as its power supply. This is how the term "completely portable" is used herein, namely, that the unit is a fully self-contained, hand-held unit. Unlike in the first embodiment, there is no connecting cable connecting the probe to a control box. The power supply and all controls are built into the hand-held ESD that in one design, is shaped with a slight bend for the holding area that is built into the probe part of the device. In another design, the hand-held section is formed more towards a right angle with the probe, somewhat like a pistol, with a pistol-type grip for holding the ESD and a trigger, similar to that of a pistol, as the button for controlling the ESD in the performing the treatment procedure. The probe can be formed as a single piece with the hand-holding part of the ESD. Alternatively, the probe is formed as detachable with the hand-holding part of the ESD so that a probe can be disconnected for cleaning, disinfecting or sterilization and for compact storage and ease of travel, and reconnected with either the same or a different probe. The described unit is therefore in one embodiment is autolockable by being subjected to a heat cycle to sterilize the unit. In addition, in another embodiment the battery pack 2011 is removable for replacement between procedures while the other battery pack is being recharged in an adapter charger.

Figure 21:
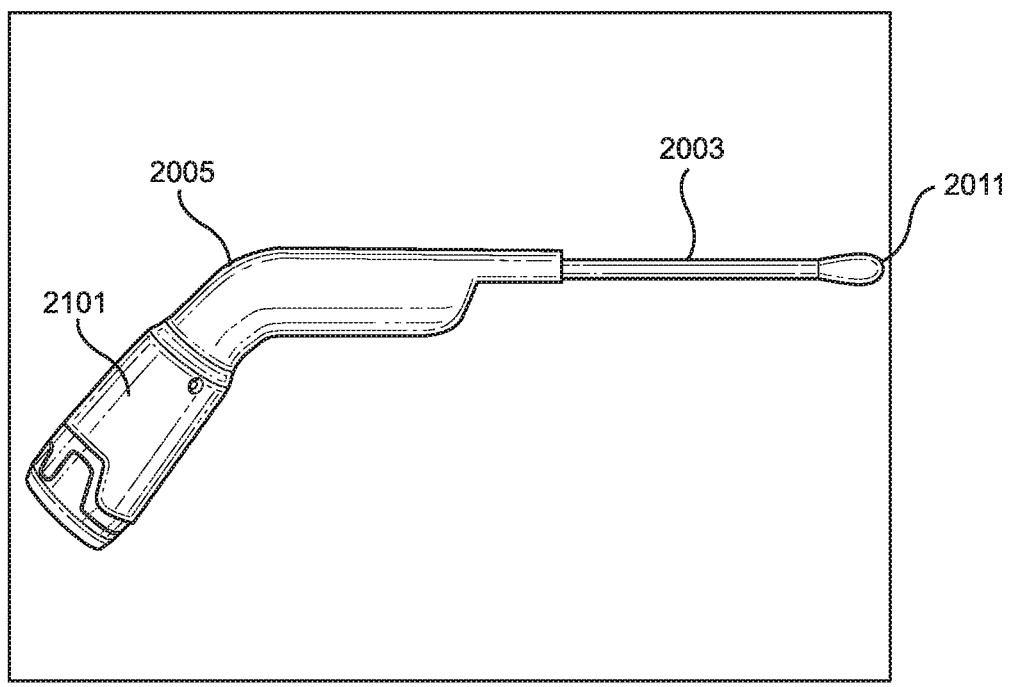
FIG. 21 is a side view of the ESD of FIG. 20.

The perspective view of FIG. 20 shows an ESD 2001 in one aspect according to the second embodiment. ESD 2001 contains a probe 2003, a one-button operation control button 2005, a low battery indicator light 2007, a status indicator light 2009 and a probe tip or simply a tip 2011. FIG. 21 is a side view of the ESD of FIG. 20. In FIG. 21, components common to those shown in FIG. 20 are given the same numbers as in FIG. 20, namely tip 2011, probe 2003 and one button operation control button 2005. FIG. 21 also shows probe handle 2101 which is partially visible in the front perspective view of FIG. 20. Additional LED indicators can display a timing count-down for the approximate one minute procedure time application.

Control button 2005 operates with the following functions:

Pressing control button 2005 turns the ESD on, electricity is activated, and the USD waits for a switch to activate the heating element by sending electric current to the heating element. An LED light appears on status indicator light 2009 to confirm to the user that the ESD is ready to use on the patient.

Pressing control bottom 2005 again initiates the treatment cycle with the heating element activated for starting and continuing the treatment on the patient. A blue light appears on status indicator light 2009 to confirm to the user that current is being delivered to the heating element or, in other words, the heating element is heated to a predefined working temperature for use in proceeding with the treatment. Additional LED indicators can display a timing count-down for the approximate one minute procedure time application.

After the treatment is over, and the probe is removed from the patient's body, such as from the vagina of a female patient, an extended pressing of control button 2005 initiates a sanitization process of tip 2011. In the sanitization process, an elevated temperature is generated in the tip for a predetermined period of time to kill bacteria, viruses and/or other material adhering to the tip. A cleaned, sterilized tip results, ready for use on the next patient.

In another embodiment, a secondary emergency shut off button, not shown, is added on the probe.

Probe and Tip Features

Figure 22:
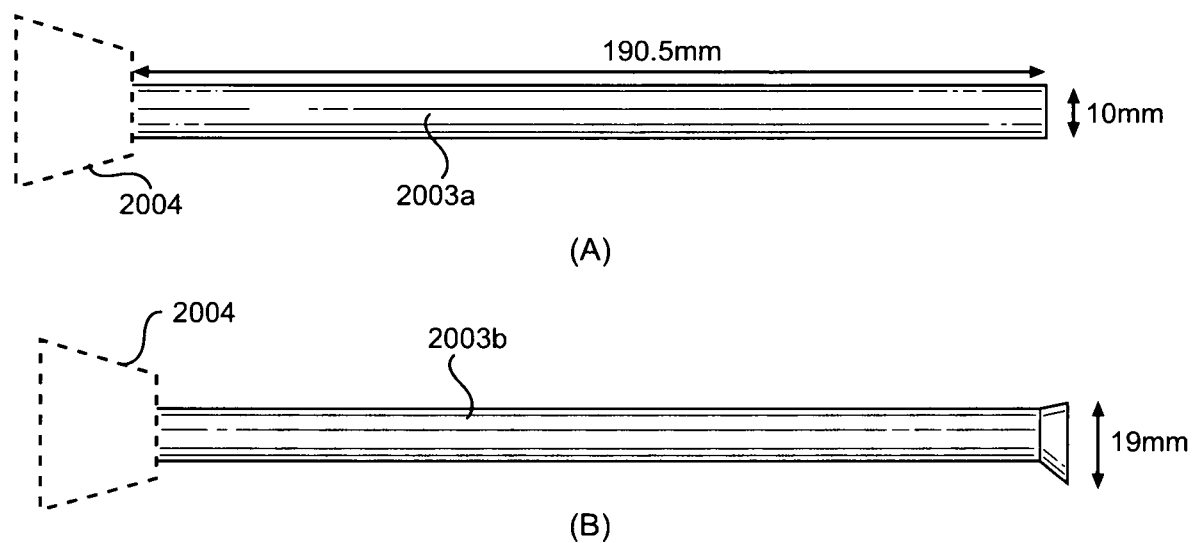
FIGS. 22(A)-(B) are side views of a probe and depict two different size versions of the probe.

FIGS. 22(A)-(B) are side views of probe 2003 depicting two different size versions of the probe. Part 2004 in dashed lines on each drawing illustrates that the probe is connected to another part of the ESD. This other part 2004 in the ESD of the first embodiment is a first type of handle which is connected by a cable to the ESD housing. This other part In the ESD of the second embodiment is a second type of handle in which the ESD electronics and power supply are located.

In FIGS. 22(A) and 22(B), the shape of the probe, probe 2003a and 2003b respectively, is the same, namely circular, and the length of each probe is the same, 175 millimeter (mm) in one version of the probe's length. However, the tip diameter of each probe is different. The tip in FIG. 22(A) has a diameter of 10 millimeters (mm), while the tip in FIG. 22(B) has a diameter of 19 mm. Both tips could have a center nipple that rises ~5 mm from the flat surface on the distal tip end (shown in FIG. 27(B)). The bump or nipple-shaped center part of the tip helps to locate the cervical center opening (external cervical). On the other hand, a flat tip surface without the nipple is of benefit in other situations such as by being able to be easily moved to wherever the lesion is on the cervix, such as across the transformation zone, etc. Having this choice of two different tip shapes or more gives an advantage to the user for more effective treatment since a precise tip can be selected based on the localized use of the ESD, such as in treating in the canal and other specific locations.

Regulated Temperature

The heating element is contained within the tip, transparent to the user. Typically, the wattage dissipated at the heating element is approximately 40-50 watts with a voltage of ~9 volts regulated, a resistance of approximately 2.0 ohms and a current of 4-6 amps. For example, with power P (watts)=voltage V (volts) x current I (amps), if V=9 volts and I=9 amps, the P=45 watts. The ESD typically uses a 12-volt lithium ion battery that is regulated down to 9-10 volts to the heating element.

The operating values of P, V, I and resistance R are constant when the controller is applying the voltage to the heating element. However, either a PTC control or a feedback circuit that senses the temperature in a thermistor or other temperature sensor at the tip limits the current and gives feedback of what the temperature is and turns the voltage ON or OFF to control the temperature as needed to, say, 100-120° C. or whatever is set into the controller. Because the temperature control has a slight delay, the temperature typically cycles within a few degrees.

Programmable Functions

The controller has a "control point" setting that controls the temperature of the heating element. This is typically set for 100-120° C. but does have a variable setting. The temperature of the heating element and the tip is essentially the same due to the close proximity of the tip to the heating element and the high thermal conductivity material used in the tip, such as copper, aluminum, or special ceramic substances. As regards the variable setting, this feature in the controller allows for the operating parameters, such as power, voltage, current, and the like, to be changed by being programmed into the micro-controller (the terminology of controller, microprocessor, micro-controller and computer are all used interchangeably in describing features of the controller). These variables can be programmed, similar to the manner in which items are programmed in a hand-held device, such as a mobile phone for example. A simple program uses this programmed information based on inputs from a membrane switch, a connectable keypad and the like.

Figure 23:
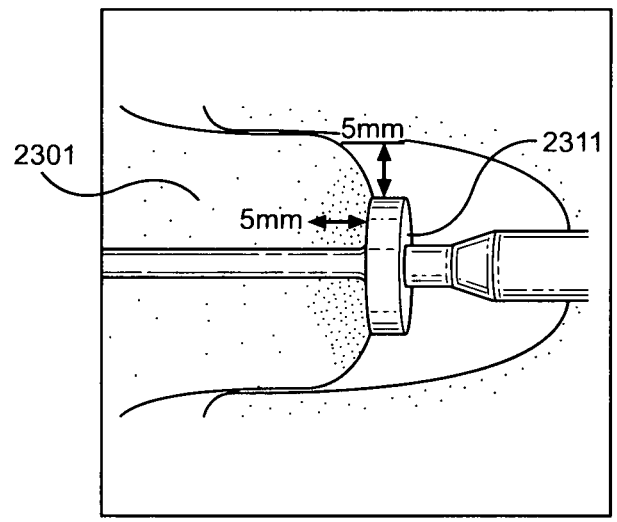
FIG. 23 is an illustration of a tip making contact with the targeted tissue during a treatment.

FIG. 23 is an illustration of tip 2311 making contact with the targeted tissue during a treatment. The heat from the tip effectively destroys the tissue down to an average depth of 5 mm, and a width, measured laterally outside of the sides of the tip, of 5 mm. FIG. 23 shows an example of the probe tip containing the heating element against, for example, the cervix, heating it as a further example, to 120° C. and ablating tissue to a depth of 5 mm and width of 5 mm.

Figure 24:
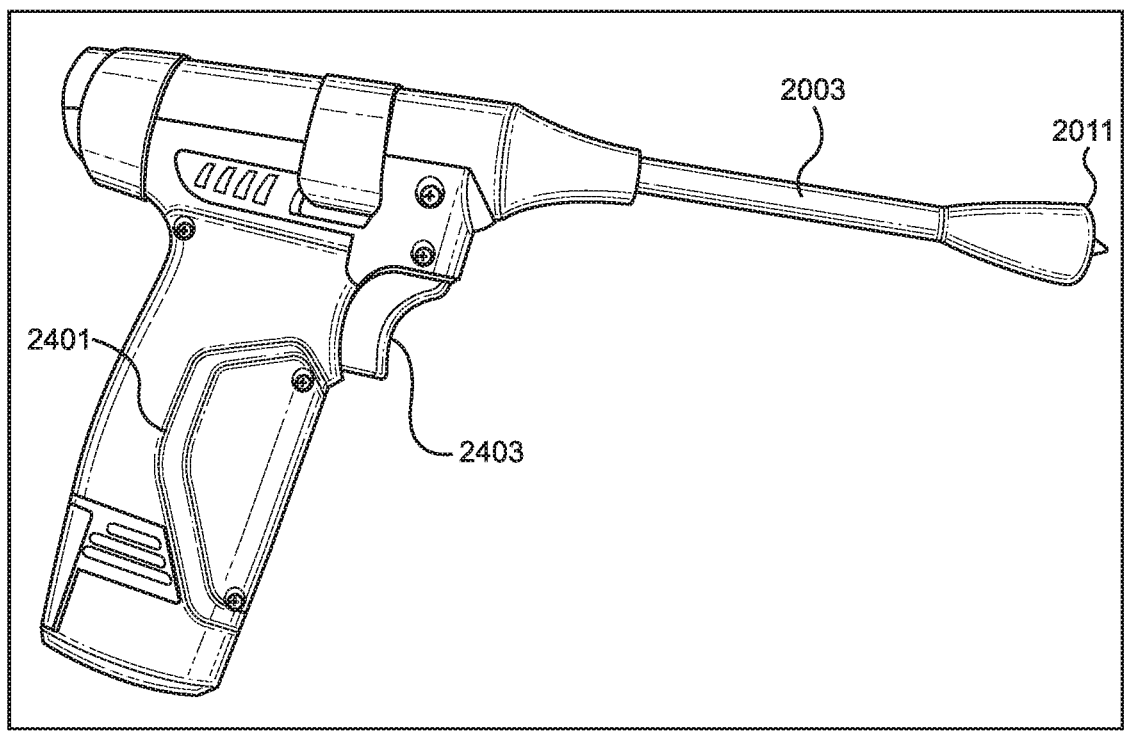
FIG. 24 shows a side view of a different aspect of the ESD according to another embodiment.

FIG. 24 shows a side view of a different aspect of the ESD according to the second embodiment. In FIG. 24, the ESD has a probe 2003 with a tip 2011 attached to the distal end of the probe 2003. In this aspect of the ESD, the handle 2401 forms an angle close to a right angle with probe 2003 and the user grips the handle 2401 much like the grip on a pistol. A finger switch 2403 is positioned akin to the trigger on a pistol. Finger switch 2403 can perform a similar function to control button 2005 in FIG. 20 or finger switch 2403 can be an emergency shut off switch, which was discussed with respect to FIG. 20 but not shown in that figure.

Different from the first embodiment, in the second embodiment, there is no housing component and no cable connecting a housing component to the probe. In the second embodiment the entire ESD is compactly provided in a one piece unit with a shape, in one aspect, resembling that of a pistol, having a hand grip or "handle" connected to the probe. While the ESD of the second embodiment is a one piece unit, components of the unit can be disconnected according to one aspect of the second embodiment, such as the ESD of FIG. 24. The one piece with detachable components of the second embodiment makes the ESD very compact with respect to its transport and in its usage.

Figure 25:
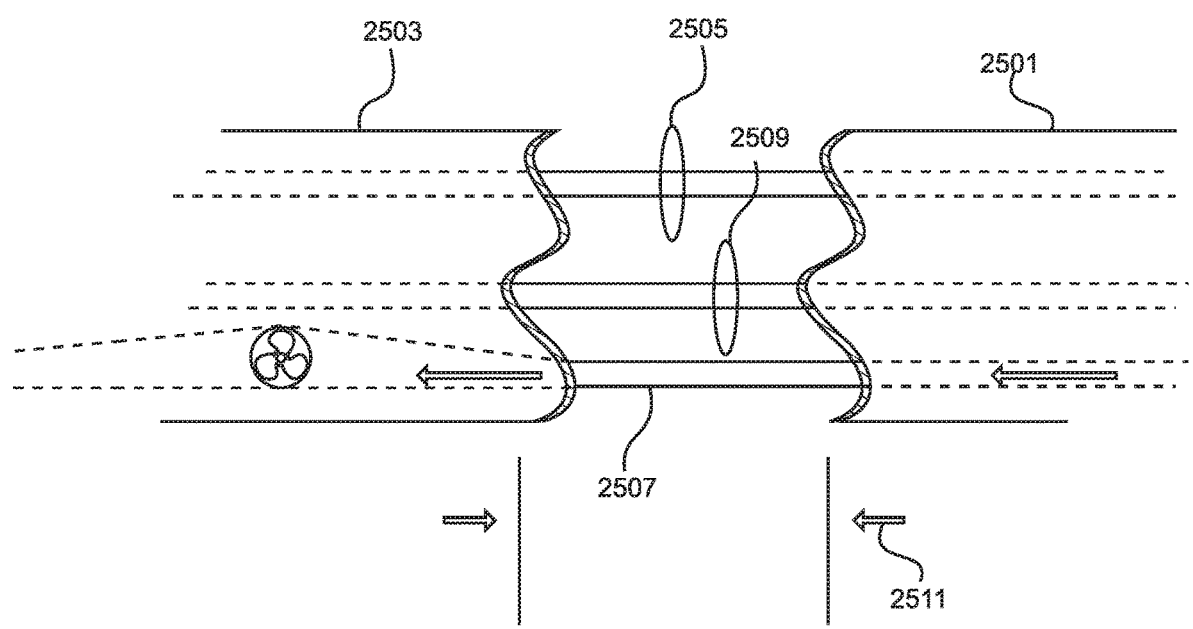
FIG. 25 is as illustration of a probe disconnected from the handle of the ESD and the associated wiring and conduit connections of various features described.
Figure 26:
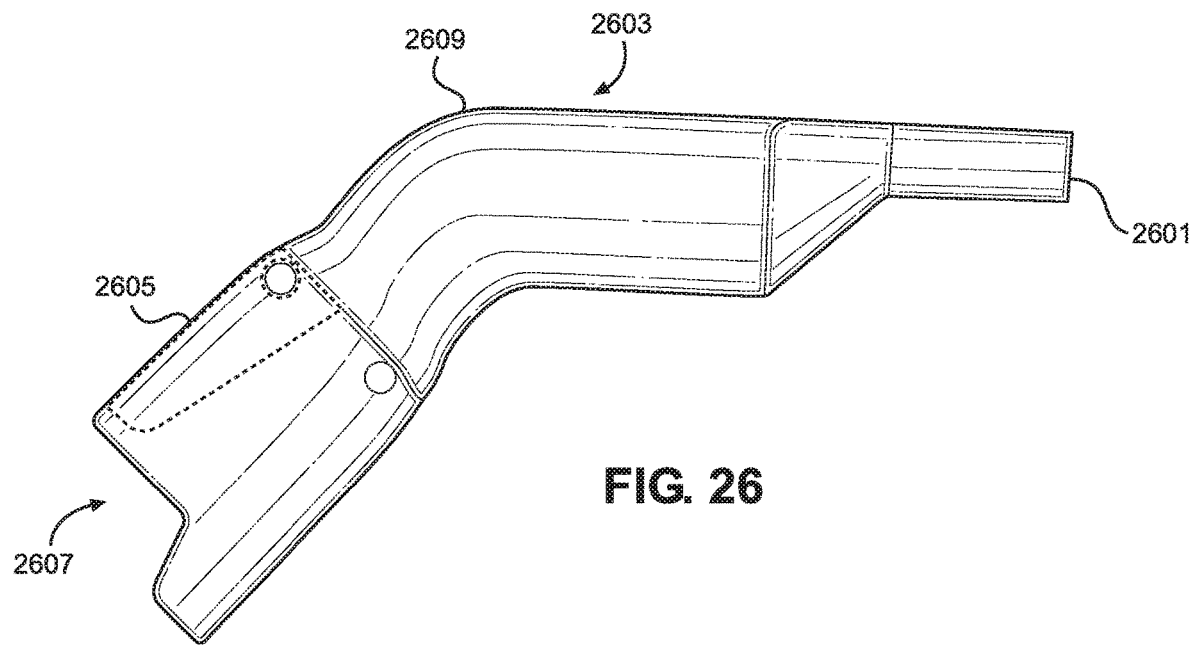
FIG. 26 is another embodiment in which the ESD is formed as a one-piece, integral unit.
Figure 27:
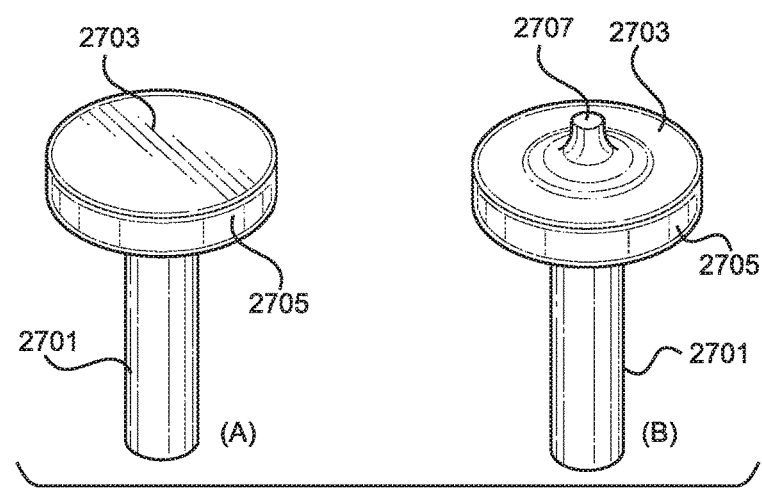
FIGS. 27(A)-(B) show two types of tips usable with any version of the described ESDs.

In one aspect of the second embodiment, probe 2501 is directly, but detachably, connected to handle 2503, such as shown in FIG. 25. In another aspect of the second embodiment, probe 2501 and handle 2503 are integrally formed as one piece, such as shown in FIGS. 26-27. In both aspects, the handle houses the electronic circuitry, one or more memory components and controllers (also referred to as a computer or microprocessor), and the one or more rechargeable batteries. The end part of the handle is snap-opened, or latch-opened, to access any of these components. The handle also contains a battery charge input connector for recharging the batteries or can be a removable, rechargeable battery pack.

FIG. 25 is as illustration of a probe disconnected from the handle of the ESD and the associated wiring and conduit connections of various features described. By being able to disconnect probe 2501 from handle 2503, the user has the capability to sterilize the probe then reconnect it to the handle, or can change the probe to attach a different probe. A related aspect is that the tip (not shown in FIG. 25) can be disconnected from probe 2501. By being able to disconnect the tip, the user can sterilize the tip and then reconnect it to probe 2501, or the user can replace the tip, which contains the heating element, with a different tip that can contain a different type of heating element.

Referring to FIG. 25 and the dis-connectable probe feature, the connector for making the probe detachable can be a screw-on or a snap-on type connection, or other known type of connection to make probe 2501 removable from, and re-connectable to, handle 2503. In this aspect where probe 2501 is removable from handle 2503, the disconnect mechanism has to include connectors for making dis-connectable connections of wiring 2505, shown as two conductors, that delivers current to the heating element that is built-in to, and made a part of, the tip (not shown in FIG. 25). The probe-handle dis-connectable connection must also have a dis-connectable connection for tubing 2507, or other conduit, used in the smoke evacuation system or fluid cooling system, and for wiring 2509 used to send the signal from the temperature sensor located in the area of the tip to monitor the temperature at the tip. These dis-connectable connections are needed if either or both of these two features, namely the smoke evacuation system and the temperature monitor feature, both of which are optional, are included in the ESD of the second embodiment.

If the option of the illumination at the tip area where the treatment is performed is incorporated into the ESD, then a transmission path, such as an optical fiber or an electrically conductive pair of wires, is added to the detachable connector and the probe-to-handle connector will have a detachable connector also for that illumination feature, although this is not shown in FIG. 25. Any of the conventional types of disconnect connections can be used. FIG. 25 illustrates the various wirings and conduit components, with a cut-away view to depict the disconnect area 2511 of handle 2503 and probe 2501, and does not show a type of detachable connector which can be any one of numerous known types, such as screw-on and snap-on connectors. The electrical connector can take the form of a circular male/female connector such as a standard audio jack thus providing a connector system that does not require circular orientation.

FIG. 26 is another version of the second aspect of the second embodiment in which the ESD 2603 is formed as a one piece, integral unit made of plastic or other suitable material. A removable, rechargeable battery that would be a part of the integral unit is not shown in the figure. The electronics that includes an RF signal generator if installed is also not visible in FIG. 26 because it is further up in the handle. The electronics could be an electronics module that can be inserted, such as with a "snap-in" or other type connection, and replaced with a different electronics module, such as with a different drive signal frequency selected for use based on the tissue and characteristics of the tissue targeted for the treatment to be conducted.

A probe tip would be attached to the distal end 2601 of the probe portion. Handle portion 2605 has an opening 2607 at the base of the handle portion for inserting the battery or battery pack, and for access, if needed, to the electronic controls, circuits and memory components. The electronics part of the ESD (the memory components, controller components, electronic circuits and switches, sensors and indicators) are permanently built into the ESD of FIG. 26. However, as an alternative, the electronics part can be inserted, such as on a circuit board or as a snap-in module, that allows it to be removed or replaced.

The closure part of the base of the handle can be built as part of the battery pack so that when the battery is inserted, it snaps shut to the handle portion. Alternatively there could be a flip panel that opens to remove the battery or other parts that are mounted/stored inside the handle and that flips shut to close. Portion area 2609 is where membrane switches are positioned for finger control by the user.

Once the battery pack is inserted into the handle and the tip is attached to the end of probe portion 2601, the compact unit is ready for use.

FIGS. 27(A)-(B) show two types of tips usable with any version of the described ESDs. FIG. 27(A) has an extension 2701 that is insertable or otherwise attached to the distal end of the probe. At the top end of the extension is a flat circular tip surface 2703 that defines an area that is heated, and a tip side 2705 that defines a depth or thickness of the tip. The area of tip surface 2703, or at least a part thereof, is placed in contact with the targeted tissue of the patient during the treatment. FIG. 27(B) is similar to FIG. 27(A) and like components thereof are not repeated. The difference in the tip of FIG. 27(B) is the centered projected region or nipple 2707. This gives a more focused or sharp point for focusing the heat at a pivotal point of the subject tissue.

Figure 28:
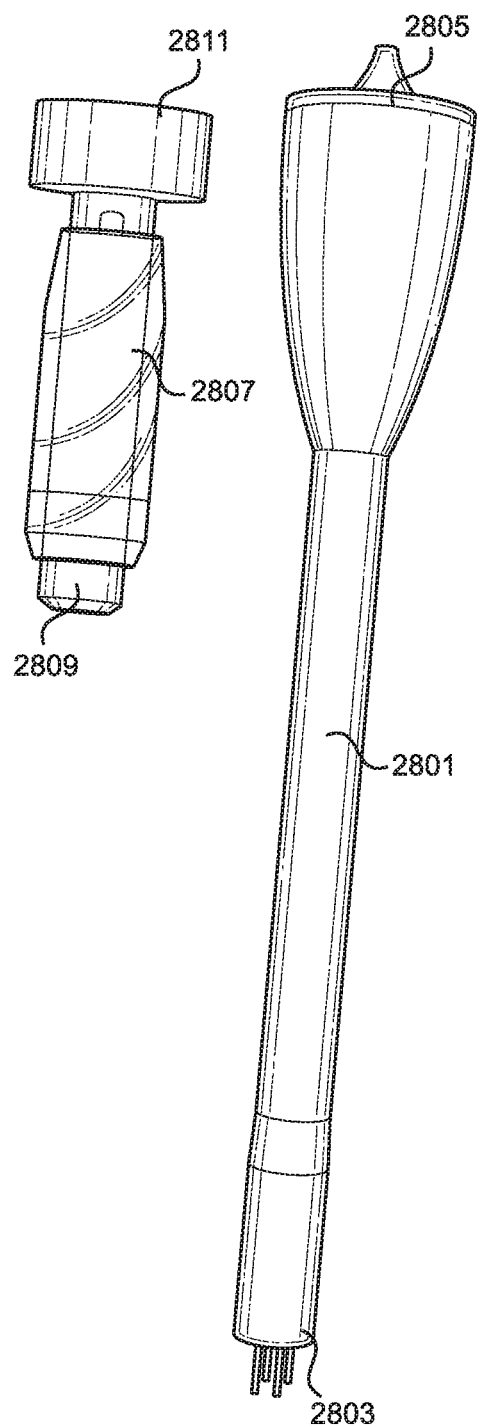
FIG. 28 shows a detached probe with a nipple tip of FIG. 27(B) attached to the distal end of the probe.

FIG. 28 shows a detached probe 2801 with a nipple tip of FIG. 27(B) attached to the distal end of the probe. The opposing end 2803 of probe 2801 is inserted into a handle or other hand-holding component of the ESD. Next to the probe with the attached nipple tip is a "flat head" tip component, as shown in FIG. 27(A), with its heated tip part 2811, an intermediate shaft part 2807 and its opposite end part 2809. End part 2809 would be inserted into, or otherwise attached to, the probe.

Figure 29:
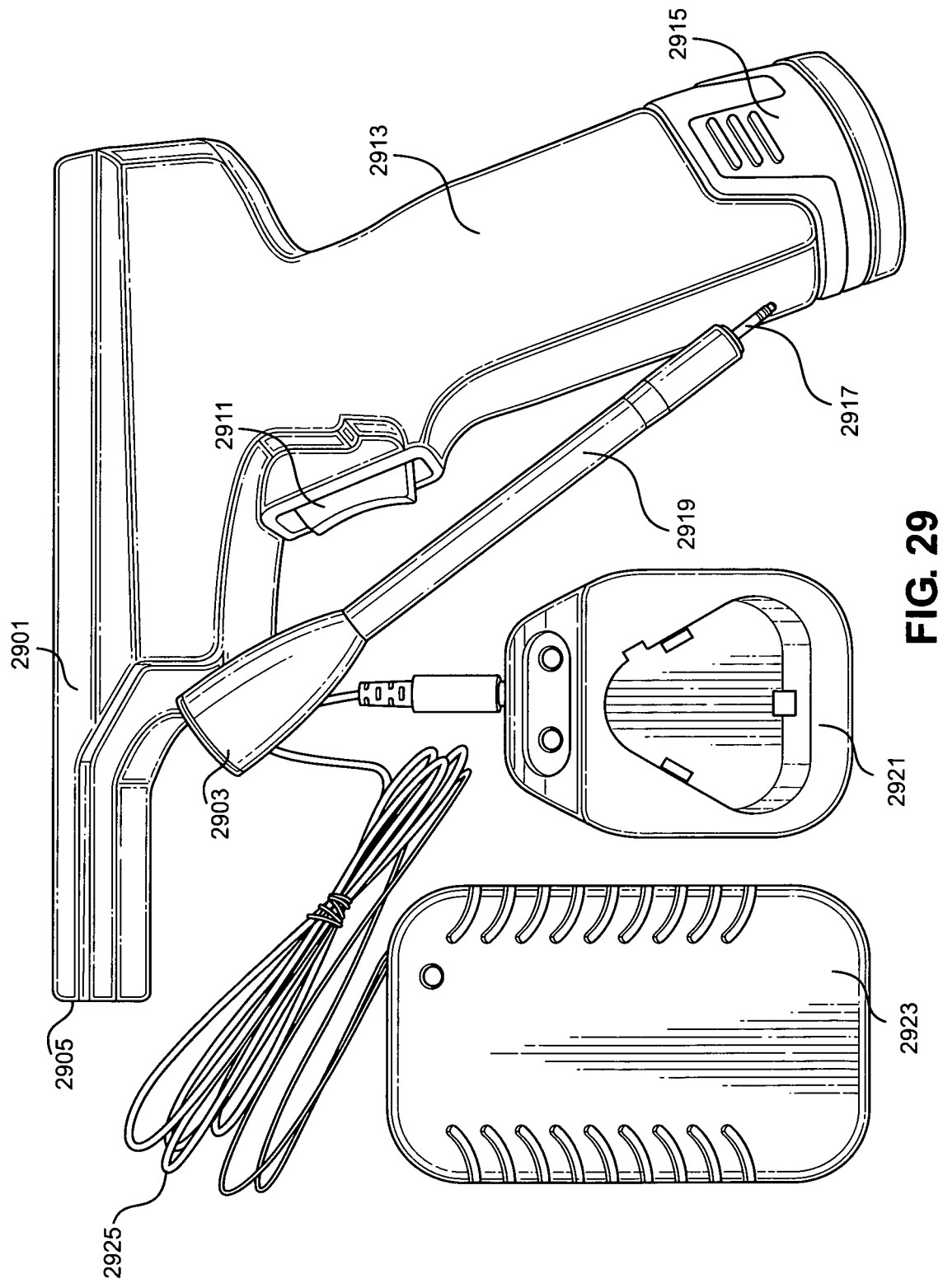
FIG. 29 shows an entire portable, hand-held ESD unit.
Figure 30:
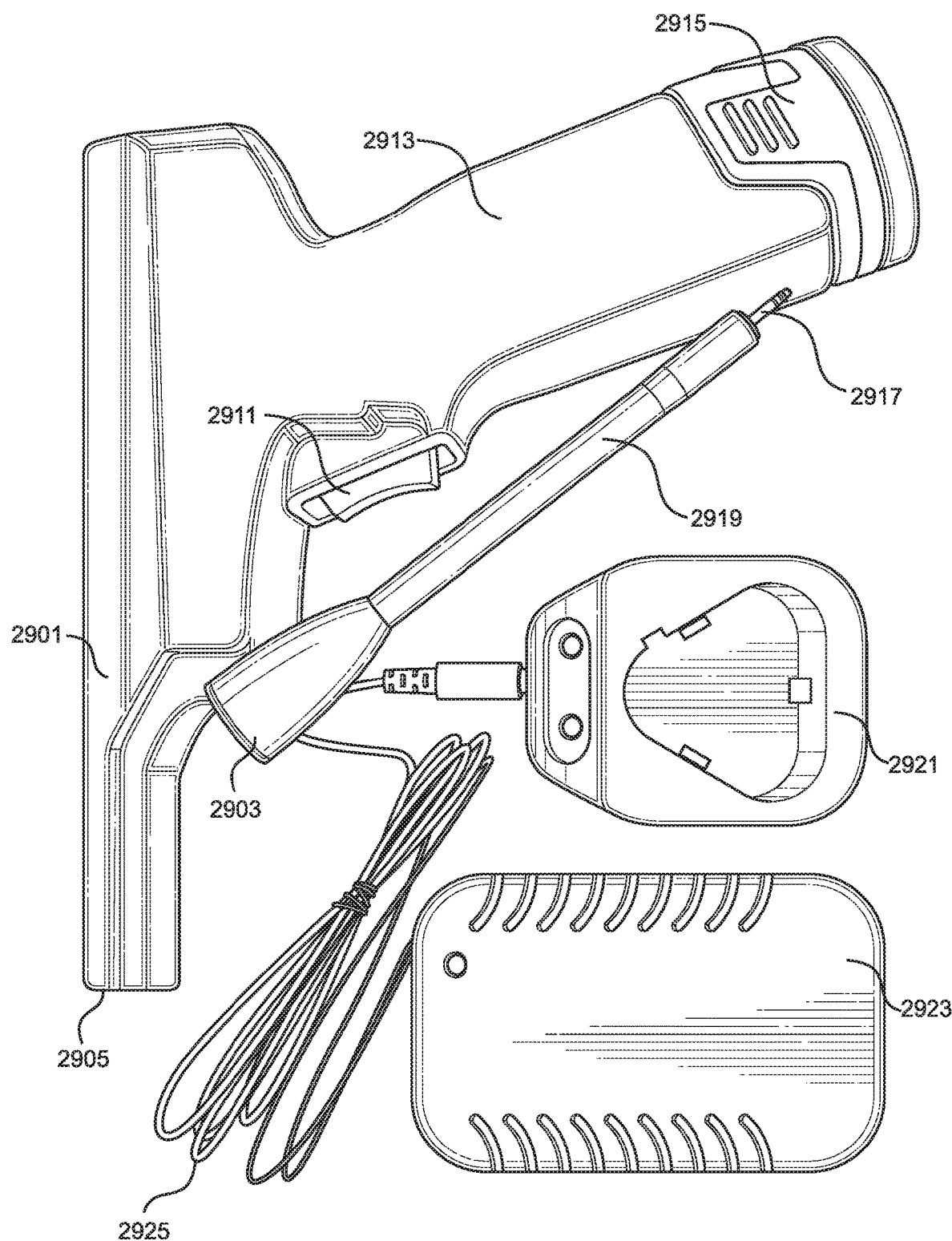

FIG. 29 shows an entire portable ESD unit according to the second embodiment. The one piece integrally formed body is formed resembling a pistol shape and has a switch 2911 that is activated with the trigger finger. This trigger switch can, for example, be used to turn the heat delivery system ON and OFF to control heat delivered to the tip. In FIG. 29, probe 2919 has the tip 2903 connected to the probe but the probe is disconnected from the body of the ESD. The probe 2919 is attachable by mating end 2917 of probe 2919 to end 2905 of the body 2901 of the ESD.

The ESD has a handle 2913 formed downward from the probe approaching a right angle being formed between the two components, although it is seen that the slant of the handle of this ESD forms an angle that is something less than a right angle. The base 2915 of handle 2913 is a removable, exchangeable, rechargeable battery pack. The end of the base 2915 of handle 2913 is shaped in roughly a triangular shape and can be removed and replaced so it can fit into re-charge station 2921 with connection pins for recharging. The re-charge station 2921 is connected by a conductive cable, comprising a pair of conductive wires, to an AC to DC adapter for converting AC power to DC power and output a DC voltage at a level compatible for recharging the rechargeable batteries used in the portable, hand-held ESD. Another lead from the AC to DC adapter is an AC plug (not shown) that is plugged into an AC 110-120 VAC power output, such as a wall socket connected to an electric grid.

The ESD of FIG. 29 thus provides a small, compact and portable ESD that can provide a controlled or constant temperature heating of the tip using as thermistor feedback circuit, with options of illumination on the treatment tissue area, smoke evacuation and finger-tip control through membrane switches mounted on the ESD, with up to approximately 30, 1-minute treatments able to be conducted on each battery charge.

Camera Attached to the ESDs Probe for Real-Time Viewing

In an optional aspect of both the first and second embodiments, the described ESD apparatus and method can have a miniature camera attached to the distal end of the probe to capture the environment of the surgery and transmit it to the electronics of the ESD. The video signal can then be communicated via a connecting cable, or wirelessly, to a monitor for real-time viewing by the user or others present during the surgical procedure. Bluetooth (BLE) is one known technology for communicating data over short distances, using the UHF radio waves in the 2.4 to 2.485 GHz band. Wi-Fi is another known technology for accessing a local wireless network using the 2.4 gigahertz URF band and the 5 GHz SHF radio band.

The video signal can be sent from the camera to the ESD electronics via fiber optic tubes or via electrical conductive cable. From the ESD's electronics module, the video can be connected by cable to a nearby monitor, such as is shown in FIG. 10(A).

If a wireless coupling is used in sending the signal to a local or a remote monitor, Wi-Fi is preferred because BLE is unreliable for medium bandwidth streaming due to its characteristic design for smaller data packets, with time intervals in-between. Its advantage in being used with a portable battery powered device is that BLE is a low energy technology.

On the other hand, Wi-Fi is more reliable and allows the information (video data) to be networked. Wi-Fi systems operate in accordance with the IEEE 802.11 standard and known types of 802.11 compliant products include video probes suitable for use in medical surgery. For example, endoscopic surgery is performed with a tubular probe called an endoscope that has a tiny camera and a bright light attached. The camera is inserted with the probe, and video signals are transmitted back to the monitor, such as by fiber optic tubes, while the user, and any others present, can watch in real time. See, e.g., http://www.regionalphysicianobgyn-.com/regional-physician-specialists-ob-un/health-libraryl/plastic-surgery-techniques-30586.aspx. Last accessed on Apr. 27, 2015.

The camera can be attached to the distal end of the probe in either the ESD of the first or second embodiments and the various aspects of both as described herein.

WiFi Input from a Cellular Phone to the ESD

In another aspect of the ESD of both the first and second embodiments, a Wi-Fi input from a cellular phone can be the source of an input to the ESD. In the first embodiment in particular, this wireless input would be used as an alternative to the keyboard or other input through the USB port on the housing.

While various embodiments of the present disclosure have been described above, it should be understood that they have been presented by way of example only, and not limitation. It will be apparent to persons skilled in the relevant art that various changes in form and detail can be made therein without departing from the spirit and scope of the disclosure. Thus, the breadth and scope of the present disclosure should not be limited by any of the above-described exemplary embodiments, but should be defined only in accordance with the following claims and their equivalents

The invention claimed is:

1. An electrosurgical device comprising:
   a housing;
   a probe configured to be connectable to the housing, the probe further comprising:
      a proximal end configured to be adjacent the housing when the probe is connected to the housing;
      a thermistor;
      a thermistor feedback circuit;
      a distal end configured to be adjacent tissue of a patient, the distal end further comprising:
         a heating element configured to receive a drive signal from the housing when the probe is connected to the housing; and
         a tip connected to the heating element;
   an input component disposed within the housing or the probe, the input component configured to receive an input, the input comprising a characteristic of the drive signal, the drive signal configured to be sent from the housing to the probe;
   a switch configured to receive a second input, the second input comprising instruction to send the drive signal from the housing to the probe; and
   the housing further comprising:
      a battery; and
      electronic controls configured to:
         receive the characteristic of the drive signal from the input component;
         receive the thermistor feedback from the thermistor feedback circuit;
         regulate power transferred from the battery to the probe at operating levels, at least one of the operating levels comprising a full-rated operating level configured to transfer the power from the battery at a maximum level capable of the battery; and
         send, immediately upon the switch receiving the second input, the drive signal at the full-rated operating level from the housing to the probe, the drive signal based on the received characteristic of the drive signal, the received thermistor feedback, and the full-rated operating level.

2. The electrosurgical device as in claim 1, wherein the input component comprises:
   a drive-signal selector switch configured to enable drive-signal input, the drive-signal input comprising selection of or modification of a pre-programmed drive signal to send to the heating element; and
   a signal-modification control configured to:
      activate in response to the drive-signal selector switch receiving the drive-signal input to modify the pre-programmed drive signal; and
      enable the modification of the pre-programmed drive signal to form a modified drive signal to send to the heating element.

3. The electrosurgical device as in claim 1, wherein the input component is configured to:

modify a frequency, a waveshape, a duty cycle, a voltage, or a current of the drive signal sent from the housing to the heating element;

modify a duration of time in which the drive signal is sent from the housing to the heating element;

modify a temperature setting or a temperature range to be maintained at the heating element or the tip; or turn on or off the electrosurgical device.

4. The electrosurgical device as in claim 1, wherein the heating element comprises a resistance heating element, a microwave heating element, a laser heating element, a ferromagnetic material heating element, or an ultrasound heating element.

5. The electrosurgical device as in claim 1, further comprising: comprising a smoke evacuation unit comprising:

an evacuation conduit for evacuating smoke or other airborne impurities away from a site, the evacuation conduit having a first end with a first opening, a second end with a second opening, and a middle section integrally formed with and between the first and second ends, the evacuation conduit located along at least a part of a length of the probe; and a vacuum-creating system located at least in part in the evacuation conduit and configured to withdraw air comprising the smoke or the other airborne impurities from the site through the first opening of the evacuation conduit, carry the smoke or the other airborne impurities through the middle section of the evacuation conduit, and expel the smoke or the other airborne impurities through the second opening to an outside area located away from the site; and an on-and-off switch configured to activate or deactivate the smoke evacuation unit and wherein the smoke-evacuation unit is configured to be activated automatically based on the drive signal being sent from the housing to the heating element, activated based on a second drive signal from the housing, or activated when an air sensor located near the first opening senses the smoke or other airborne impurities above a threshold level.

6. The electrosurgical device as in claim 1, wherein the housing further comprises a memory storage component containing a pre-programed modifiable signal configuration and a modifiable signal parameter and wherein receipt of the input via the input component comprises selection of the pre-programmed modifiable signal configuration or the modifiable signal parameter as the characteristic of the drive signal configured to be sent to the heating element.

7. The electrosurgical device as in claim 1, further comprising a camera or a display connected to the housing or the probe, wherein:

the camera or the display is configured to help diagnose disease for treatment;

the camera is configured to take images for storage or display on the display; or the display is configured to view the tissue of the patient or a stored image.

8. The electrosurgical device as in claim 7, further comprising a wireless transmission component and wherein data captured by the camera is transmitted by the wireless transmission component via a wireless transmission protocol.

9. The electrosurgical device as in claim 1, further comprising an emergency button configured to stop a transfer of power to the heating element, the emergency button positioned within a reach of a finger of a user holding the electrosurgical device during a treatment.

10. The electrosurgical device as in claim 1, further comprising:

a light-emitting element configured to cast illumination onto a site;

a second switch configured to control an operation of the electrosurgical device, the second switch comprising a membrane switch, a mechanical switch, or a foot switch; and a light indicator configured to provide a visual indication of a state of the second switch, the light indicator comprising a backlighting light, a discrete light, a light-emitting diode, an optical fiber, or an electroluminescent light.

11. The electrosurgical device as in claim 1, further comprising:

a timer for measuring and providing time data;

the battery comprising a rechargeable battery configured to be removable from the housing and replaceable by another rechargeable battery, the rechargeable battery comprising a lithium ion battery or a lithium polymer battery;

a power sensor for detecting a state of the battery;

a light configured to illuminate an area near the distal end of the probe, the light comprising an end-emitting optical fiber with an end-emitter fixture attached, a side-emitting optical fiber, or a combined end-emitting with end-emitter fixture and side-emitting optical fiber;

a light indicator visible during a treatment of the patient and operably connected to the timer, the power sensor, or the light:

a membrane switch that, responsive to receiving membrane switch input, causes the light indicator to indicate the time data associated with the timer, the state of the battery sensed by the power sensor, or a condition of the light;

a second light indicator visible during a treatment of the patient and operably connected to the timer, the power sensor, or the light and wherein the second light indicator is configured to automatically indicate information not indicated by the first light indicator and wherein the information comprises one of the time data associated with the timer, the state of the battery sensed by the power sensor, or the condition of the light; or a display for displaying the time data associated with the timer, the state of the battery sensed by the power sensor, or the condition of the light.

12. The electrosurgical device as in claim 1, further comprising a cooling-down system comprising:

a cooling conduit located along at least a part of a length of the probe;

a pump positioned at least in part in the cooling conduit and configured to direct fluid from an outside area through the cooling conduit to the distal end of the probe; and an aperture connected to the cooling conduit, the aperture extending outwardly from the probe and configured to allow passage of the fluid from the outside area through the aperture to an area near the distal end of the probe.

13. The electrosurgical device as in claim 1, wherein the electrosurgical device further comprises a user-input terminal configured to receive input data from a touch screen, a keyboard, a mouse, a network-connected device, a USB-connected device, or an audio-input device and wherein the electrosurgical device is further configured to display the received input data on the touch screen or a display, store the received input data in a memory storage component, receive an internet connection via the network-connected device, connect to a web site or other internet-connected computing service, display the web site on the touch screen or the display, or to store information in the memory storage component received from the web site or internet-connected computing device.

14. The electrosurgical device as in claim 1, wherein the thermistor feedback comprises a temperature measurement associated with the heating element or the tip.

15. The electrosurgical device as in claim 14, wherein the electronic controls are configured, based on the temperature measurement, to maintain a temperature of the heating element or the tip and wherein the temperature is sufficient to ablate the tissue of the patient.

16. The electrosurgical device as in claim 1, wherein the electronic controls are further configured to send the drive signal to the probe in a pulsed or an intermittent manner.

17. The electrosurgical device as in claim 16, wherein the electronic controls are further configured to maintain an operating temperature of the heating element or the tip by:
    adjusting a pulse rate or a pulse duration of the drive signal; or
    turning on or off a circuit between the battery and the heating element.

18. The electrosurgical device as in claim 1, wherein the housing further comprises a power input port and wherein the battery connects to the housing via the power input port and wherein at least a portion of the battery is external to the housing.

19. The electrosurgical device as in claim 1, wherein the heating element or the tip is configured to be detachable from the probe and wherein the probe is configured to receive another heating element or another tip.

20. A method of using an electrosurgical device comprising:
    providing the electrosurgical device, the electrosurgical device comprising:
        a housing;
        a probe configured to be connectable to the housing, the probe further comprising:
            a proximal end configured to be adjacent the housing when the probe is connected to the housing;
            a thermistor;
            a thermistor feedback circuit;
            a distal end configured to be adjacent tissue of a patient, the distal end further comprising:
                a heating element configured to receive a drive signal from the housing when the probe is connected to the housing; and
                a tip connected to the heating element;
        an input component disposed within the housing or the probe, the input component configured to receive an input, the input comprising a characteristic of the drive signal, the drive signal configured to be sent from the housing to the probe;
        a switch configured to receive a second input, the second input comprising instruction to send the drive signal from the housing to the probe; and
        the housing further comprising:
            a battery; and
            electronic controls configured to:
                receive the characteristic of the drive signal from the input component;
                receive the thermistor feedback from the thermistor feedback circuit;
                regulate power transferred from the battery to the probe at operating levels, at least one of the operating levels comprising a full-rated operating level configured to transfer the power from the battery at a maximum level capable of the battery; and
                send, immediately upon the switch receiving the second input, the drive signal at the full-rated operating level from the housing to the probe, the drive signal based on the received characteristic of the drive signal, the received thermistor feedback, and the full-rated operating level;
    receiving default drive signal information corresponding to the heating element, the default drive signal information configured to be sent from the housing to the heating element, the default drive signal information corresponding to operations of the heating element;
    receiving selection to treat the tissue of the patient using the default drive signal information or receiving selection to treat the tissue of the patient using modified drive signal information:
        if receiving selection to treat the tissue of the patient using the default drive signal information, then:
            sending, from the housing and to the heating element, the drive signal information;
            causing, according to the default drive signal information, the operations in the heating element; and
            treating the tissue of the patient, the treatment comprising application of the heating element or the tip connected to the heating element to the tissue of the patient; or
        if receiving selection to treat the tissue of the patient using the modified drive signal information, then:
            receiving, from the input component, the input, the input comprising a modified characteristic of the default drive signal information;
            modifying, based on the received input, the default drive signal information to generate the modified drive signal information, the modified drive signal information configured to modify the operations of the heating element;
            sending, from the housing and to the heating element, the modified drive signal information;
            causing, according to the modified drive signal information, modified operations in the heating element; and
            treating the tissue of the patient, the treatment comprising application of the heating element or the tip connected to the heating element to the tissue of the patient.

* * * * *